(12) United States Patent
Wilson et al.

(10) Patent No.: US 7,774,933 B2
(45) Date of Patent: Aug. 17, 2010

(54) METHOD OF MANUFACTURING ULTRASOUND CATHETERS

(75) Inventors: Richard R. Wilson, Seattle, WA (US);
Tim Abrahamson, Seattle, WA (US);
Leonard R. Oliver, Seattle, WA (US)

(73) Assignee: Ekos Corporation, Bothell, WA (US)

( * ) Notice: Subject to any disclaimer, the term of this patent is extended or adjusted under 35 U.S.C. 154(b) by 1110 days.

(21) Appl. No.: 11/417,384

(22) Filed: May 4, 2006

(65) Prior Publication Data

US 2006/0201604 A1    Sep. 14, 2006

Related U.S. Application Data

(60) Division of application No. 10/378,032, filed on Feb. 28, 2003, now abandoned, which is a continuation-in-part of application No. 10/309,417, filed on Dec. 3, 2002, now Pat. No. 7,384,407.

(60) Provisional application No. 60/361,341, filed on Feb. 28, 2002.

(51) Int. Cl.
*H01R 43/00* (2006.01)
*H05K 13/00* (2006.01)
(52) U.S. Cl. .............................. 29/854; 29/595; 29/825; 600/459; 600/463; 600/466; 600/467
(58) Field of Classification Search .................. 29/854, 29/595, 825, 857, 874; 600/459, 463, 466, 600/467

See application file for complete search history.

(56) References Cited

U.S. PATENT DOCUMENTS

| 3,433,226 | A | 3/1969 | Boyd |
| 4,040,414 | A | 8/1977 | Suroff |
| 4,176,662 | A | 12/1979 | Frazer |
| 4,319,580 | A | 3/1982 | Colley et al. |
| 4,531,943 | A | 7/1985 | Van Tassel et al. |

(Continued)

FOREIGN PATENT DOCUMENTS

DE    4005743    8/1991

(Continued)

OTHER PUBLICATIONS

Hynynen et al.; "Small Cylindrical Ultrasound Sources for Induction of Hyperthermia Via Body Cavities or Interstitial Implants", Int. J. Hyperthermia, 1993, vol. 9, No. 2, 263-274, Tucson, Arizona.

(Continued)

*Primary Examiner*—Thiem Phan
(74) *Attorney, Agent, or Firm*—Knobbe Martens Olson & Bear, LLP

(57) ABSTRACT

An ultrasonic catheter is manufactured by providing an inner tube having an inner diameter sufficient to accommodate a guidewire, and mounting a tubular ultrasound radiating member around a distal region of the inner tube. Two electrical conductors are positioned along the inner tube, such that one of the electrical conductors contacts an inner side of the ultrasound radiating member while the other electrical conductor contacts an outer side of the ultrasound radiating member. An outer tube is then concentrically translated over the inner tube and the ultrasound radiating member, and radially shrunken onto the inner tube.

7 Claims, 11 Drawing Sheets

U.S. PATENT DOCUMENTS

| | | |
|---|---|---|
| 4,549,533 A | 10/1985 | Cain et al. |
| 4,739,768 A | 4/1988 | Engelson |
| 4,750,902 A | 6/1988 | Wuchinich et al. |
| 4,808,153 A | 2/1989 | Parisi |
| 4,841,977 A | 6/1989 | Griffith et al. |
| 4,870,953 A | 10/1989 | DonMichael et al. |
| 4,906,238 A | 3/1990 | Greenfeld et al. |
| 4,920,954 A | 5/1990 | Alliger et al. |
| 4,924,863 A | 5/1990 | Sterzer |
| 4,936,281 A | 6/1990 | Stasz |
| 4,948,587 A | 8/1990 | Cost et al. |
| 5,021,044 A | 6/1991 | Sharkawy |
| 5,059,851 A | 10/1991 | Corl et al. |
| 5,108,369 A | 4/1992 | Ganguly et al. |
| 5,158,071 A | 10/1992 | Umemura et al. |
| 5,163,421 A | 11/1992 | Bernsteing et al. |
| 5,197,946 A | 3/1993 | Tachibana |
| 5,226,421 A | 7/1993 | Frisbie et al. |
| 5,250,034 A | 10/1993 | Appling |
| 5,267,954 A | 12/1993 | Nita |
| 5,267,985 A | 12/1993 | Shimada et al. |
| 5,269,291 A | 12/1993 | Carter |
| 5,269,297 A | 12/1993 | Weng et al. |
| 5,271,406 A | 12/1993 | Ganguly et al. |
| 5,282,785 A | 2/1994 | Shapland et al. |
| 5,286,254 A | 2/1994 | Shapland et al. |
| 5,295,484 A | 3/1994 | Marcus et al. |
| 5,304,115 A | 4/1994 | Pflueger et al. |
| 5,312,328 A | 5/1994 | Nita et al. |
| 5,318,014 A | 6/1994 | Carter |
| 5,327,891 A | 7/1994 | Rammier |
| 5,328,470 A | 7/1994 | Nabel et al. |
| 5,342,292 A | 8/1994 | Nita et al. |
| 5,344,435 A | 9/1994 | Turner et al. |
| 5,345,940 A | 9/1994 | Seward et al. |
| 5,348,481 A | 9/1994 | Ortiz et al. |
| 5,353,798 A | 10/1994 | Sieben |
| 5,362,309 A | 11/1994 | Carter |
| 5,363,853 A | 11/1994 | Lieber et al. |
| 5,368,036 A | 11/1994 | Tamaka et al. |
| 5,368,557 A | 11/1994 | Nita et al. |
| 5,380,273 A | 1/1995 | Dubrul et al. |
| 5,382,228 A | 1/1995 | Nita et al. |
| 5,385,148 A | 1/1995 | Lesh et al. |
| 5,421,338 A | 6/1995 | Crowley et al. |
| 5,423,797 A | 6/1995 | Adrian et al. |
| 5,427,118 A | 6/1995 | Nita et al. |
| 5,429,136 A | 7/1995 | Nilo et al. |
| 5,431,663 A | 7/1995 | Carter |
| 5,445,155 A | 8/1995 | Sieben |
| 5,447,509 A | 9/1995 | Mills et al. |
| 5,447,510 A | 9/1995 | Jensen |
| 5,454,795 A | 10/1995 | Samson |
| 5,456,259 A | 10/1995 | Barlow et al. |
| 5,458,568 A | 10/1995 | Racchini et al. |
| 5,462,523 A | 10/1995 | Samson et al. |
| 5,465,726 A | 11/1995 | Dickinson et al. |
| 5,474,531 A | 12/1995 | Carter |
| 5,496,267 A | 3/1996 | Drasler et al. |
| 5,496,294 A | 3/1996 | Hergenrother et al. |
| 5,498,238 A | 3/1996 | Shapland et al. |
| 5,503,155 A | 4/1996 | Salmon et al. |
| 5,509,896 A | 4/1996 | Carter |
| 5,514,092 A | 5/1996 | Forman et al. |
| 5,520,189 A | 5/1996 | Malinowski et al. |
| 5,531,715 A | 7/1996 | Engelson et al. |
| 5,542,917 A | 8/1996 | Nita et al. |
| 5,546,948 A | 8/1996 | Hamm et al. |
| 5,569,197 A | 10/1996 | Helmus et al. |
| 5,571,086 A | 11/1996 | Kaplan et al. |
| 5,588,432 A | 12/1996 | Crowley |
| 5,599,326 A | 2/1997 | Carter |
| 5,603,694 A | 2/1997 | Brown et al. |
| 5,606,974 A | 3/1997 | Castellano et al. |
| 5,609,574 A | 3/1997 | Kaplan et al. |
| 5,618,275 A | 4/1997 | Bock |
| 5,620,479 A | 4/1997 | Diederich |
| 5,628,728 A | 5/1997 | Tachibana et al. |
| 5,628,730 A | 5/1997 | Shapland et al. |
| 5,630,837 A | 5/1997 | Crowley |
| 5,713,848 A | 2/1998 | Dubrul et al. |
| 5,725,494 A | 3/1998 | Brisken |
| 5,728,062 A | 3/1998 | Brisken |
| 5,735,811 A | 4/1998 | Brisken |
| 5,759,173 A | 6/1998 | Preissman et al. |
| 5,782,811 A | 7/1998 | Samson et al. |
| 5,795,298 A | 8/1998 | Vesely et al. |
| 5,807,395 A | 9/1998 | Mulier et al. |
| 5,827,313 A | 10/1998 | Ream |
| 5,827,529 A | 10/1998 | Ono et al. |
| 5,836,896 A | 11/1998 | Rosenschein |
| 5,836,946 A | 11/1998 | Diaz et al. |
| 5,842,994 A | 12/1998 | TenHoff et al. |
| 5,895,398 A | 4/1999 | Wensel et al. |
| 5,916,192 A | 6/1999 | Nita et al. |
| 5,928,186 A | 7/1999 | Homsma et al. |
| 5,931,805 A | 8/1999 | Brisken |
| 5,951,494 A | 9/1999 | Wang et al. |
| 5,971,949 A | 10/1999 | Levin et al. |
| 5,976,120 A | 11/1999 | Chow |
| 5,997,497 A | 12/1999 | Nita et al. |
| 6,001,069 A | 12/1999 | Tachibana et al. |
| 6,024,703 A | 2/2000 | Zanell et al. |
| 6,024,718 A | 2/2000 | Chen et al. |
| 6,053,868 A | 4/2000 | Geistert et al. |
| 6,096,000 A | 8/2000 | Tachibana et al. |
| 6,110,314 A | 8/2000 | Nix et al. |
| 6,113,558 A | 9/2000 | Rosenschein et al. |
| 6,120,454 A | 9/2000 | Suorsa et al. |
| 6,135,971 A | 10/2000 | Hutchinson et al. |
| 6,176,842 B1 | 1/2001 | Tachibana et al. |
| 6,182,666 B1 | 2/2001 | Dobak, III |
| 6,206,831 B1 | 3/2001 | Suorsa et al. |
| 6,210,356 B1 | 4/2001 | Anderson et al. |
| 6,228,046 B1 | 5/2001 | Brisken |
| 6,235,024 B1 | 5/2001 | Tu |
| 6,241,692 B1 | 6/2001 | Tu et al. |
| 6,241,703 B1 | 6/2001 | Levin et al. |
| 6,258,080 B1 | 7/2001 | Samson |
| 6,261,246 B1 | 7/2001 | Pantages et al. |
| 6,287,271 B1 | 9/2001 | Dubrul et al. |
| 6,296,619 B1 | 10/2001 | Brisken et al. |
| 6,361,500 B1 | 3/2002 | Masters et al. |
| 6,361,531 B1 | 3/2002 | Hissong |
| 6,368,315 B1 | 4/2002 | Gillis et al. |
| 6,372,498 B2 | 4/2002 | Newman et al. |
| 6,379,320 B1 | 4/2002 | Lafon et al. |
| 6,387,035 B1 | 5/2002 | Jung, Jr. et al. |
| 6,391,042 B1 | 5/2002 | Cimino |
| 6,416,492 B1 | 7/2002 | Nielson |
| 6,423,026 B1 | 7/2002 | Gesswein et al. |
| 6,433,464 B2 | 8/2002 | Jones |
| 6,437,487 B1 | 8/2002 | Mohr, III et al. |
| 6,456,863 B1 | 9/2002 | Levin et al. |
| 6,461,314 B1 | 10/2002 | Pant et al. |
| 6,508,775 B2 | 1/2003 | McKenzie et al. |
| 6,524,251 B2 | 2/2003 | Rabiner |
| 6,524,300 B2 | 2/2003 | Meglin |
| 6,551,337 B1 | 4/2003 | Rabiner et al. |
| 6,554,801 B1 | 4/2003 | Steward et al. |
| 6,562,021 B1 | 5/2003 | Derbin et al. |
| 6,582,392 B1 | 6/2003 | Bennett et al. |
| 6,589,182 B1 | 7/2003 | Loftman et al. |
| 6,599,288 B2 | 7/2003 | Maguire et al. |

| | | |
|---|---|---|
| 6,607,502 B1 | 8/2003 | Maguire et al. |
| 6,647,755 B2 | 11/2003 | Rabiner et al. |
| 6,652,547 B2 | 11/2003 | Rabiner et al. |
| 6,660,013 B2 | 12/2003 | Rabiner et al. |
| 6,663,613 B1 | 12/2003 | Evans et al. |
| 6,676,626 B1 | 1/2004 | Bennett et al. |
| 6,692,494 B1 | 2/2004 | Cooper et al. |
| 6,711,953 B2 | 3/2004 | Hayashi et al. |
| 6,723,063 B1 | 4/2004 | Zhang et al. |
| 6,740,040 B1 | 5/2004 | Mandrusov et al. |
| 6,824,515 B2 | 11/2004 | Suorsa et al. |
| 6,855,123 B2 | 2/2005 | Nita |
| 6,979,293 B2 | 12/2005 | Hansmann |
| 7,089,063 B2 | 8/2006 | Lesh et al. |
| 2001/0037106 A1 | 11/2001 | Shadduck |
| 2001/0041880 A1 | 11/2001 | Brisken et al. |
| 2001/0047141 A1 | 11/2001 | McKenzie et al. |
| 2002/0000763 A1 | 1/2002 | Jones |
| 2002/0032394 A1 | 3/2002 | Brisken et al. |
| 2002/0055747 A1 | 5/2002 | Cano et al. |
| 2002/0087083 A1 | 7/2002 | Nix et al. |
| 2002/0099292 A1 | 7/2002 | Brisken et al. |
| 2002/0151825 A1 | 10/2002 | Rubenchik et al. |
| 2002/0188276 A1 | 12/2002 | Evans et al. |
| 2003/0023261 A1 | 1/2003 | Tomaschko et al. |
| 2003/0028173 A1 | 2/2003 | Forsberg |
| 2003/0036705 A1 | 2/2003 | Hare et al. |
| 2003/0040698 A1 | 2/2003 | Makin et al. |
| 2003/0109812 A1 | 6/2003 | Corl et al. |
| 2003/0114878 A1 | 6/2003 | Diederich et al. |
| 2003/0236539 A1 | 12/2003 | Rabiner et al. |
| 2004/0039311 A1 | 2/2004 | Nita et al. |
| 2004/0068189 A1 | 4/2004 | Wilson et al. |

FOREIGN PATENT DOCUMENTS

| | | |
|---|---|---|
| EP | 0746245 | 12/1988 |
| EP | 0668052 | 8/1995 |
| EP | 0774232 | 5/1997 |
| EP | 1090658 A1 | 4/2001 |
| EP | 1103281 A2 | 5/2001 |
| JP | 2180275 | 7/1990 |
| JP | H02-180275 | 7/1990 |
| WO | WO 89/04142 | 5/1989 |
| WO | WO 95/01751 | 1/1995 |
| WO | WO 95/26777 | 12/1995 |
| WO | WO 96/29935 | 3/1996 |
| WO | WO 97/19645 | 5/1997 |
| WO | WO 98/18391 | 5/1998 |
| WO | WO 98/48711 | 11/1998 |
| WO | WO 98/56462 | 12/1998 |
| WO | WO 01/13357 | 2/2001 |
| WO | WO 01/54754 A1 | 8/2001 |
| WO | WO 03/051208 A1 | 6/2003 |

OTHER PUBLICATIONS

Lee et al.; "Arrays of Multielement Ultrasound Applications for Interstitial Hyperthermia"; IEEE Transactions on Biomedical Engineering; vol. 46, No. 7, Jul. 1999.
PCT International Search Report; PCT/US02/38528.
The International Search Report for PCT/US03/06462.

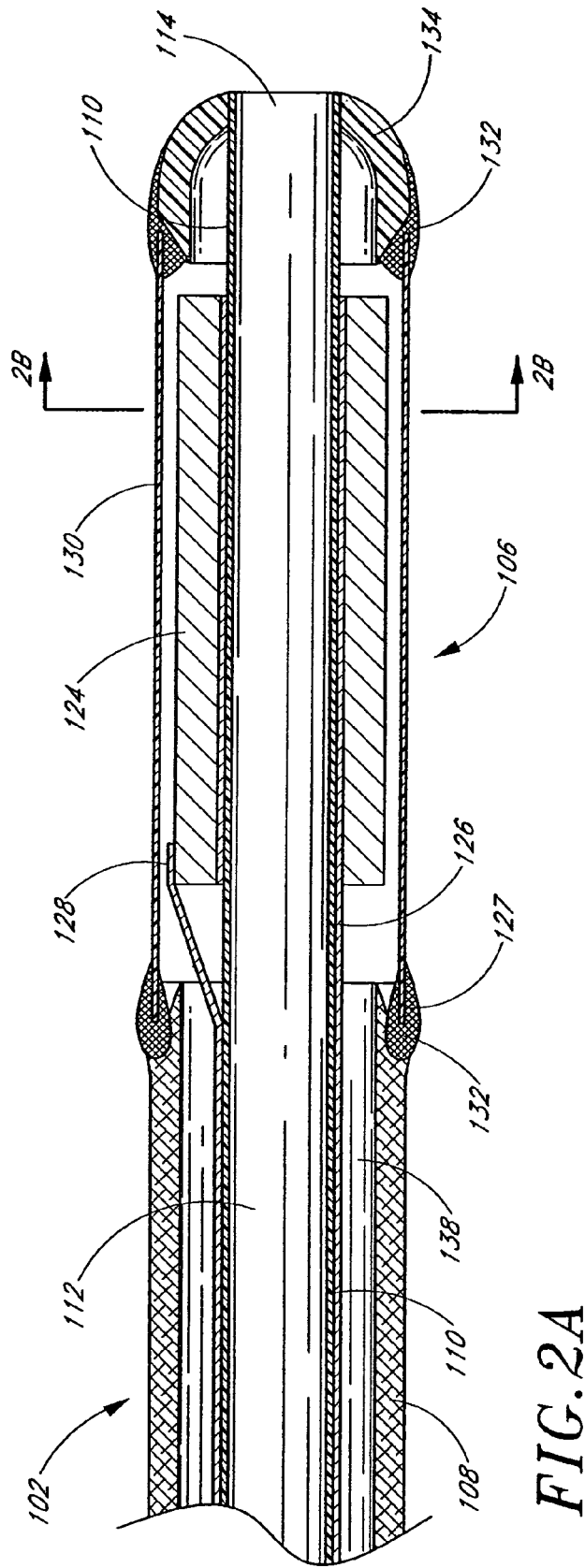
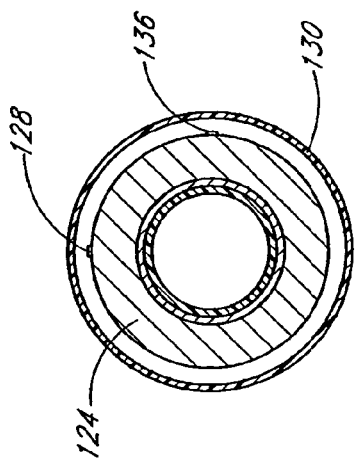
FIG.2A
FIG.2B

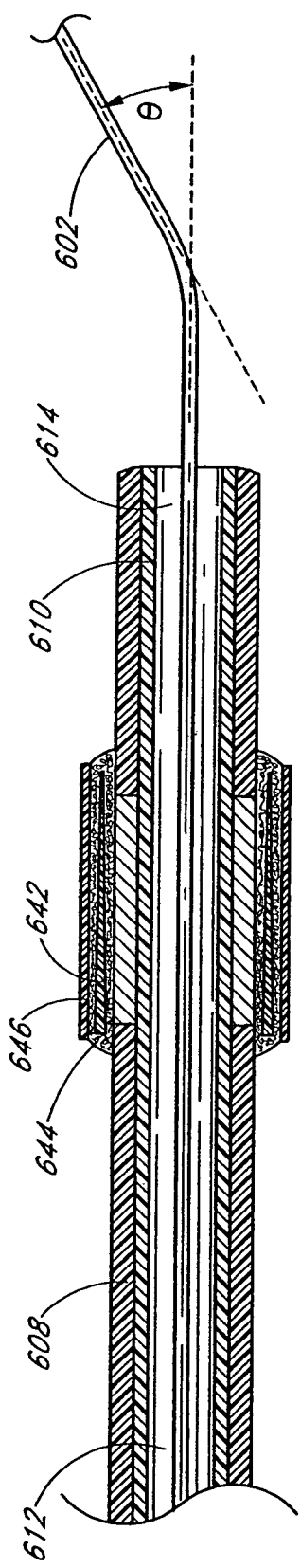
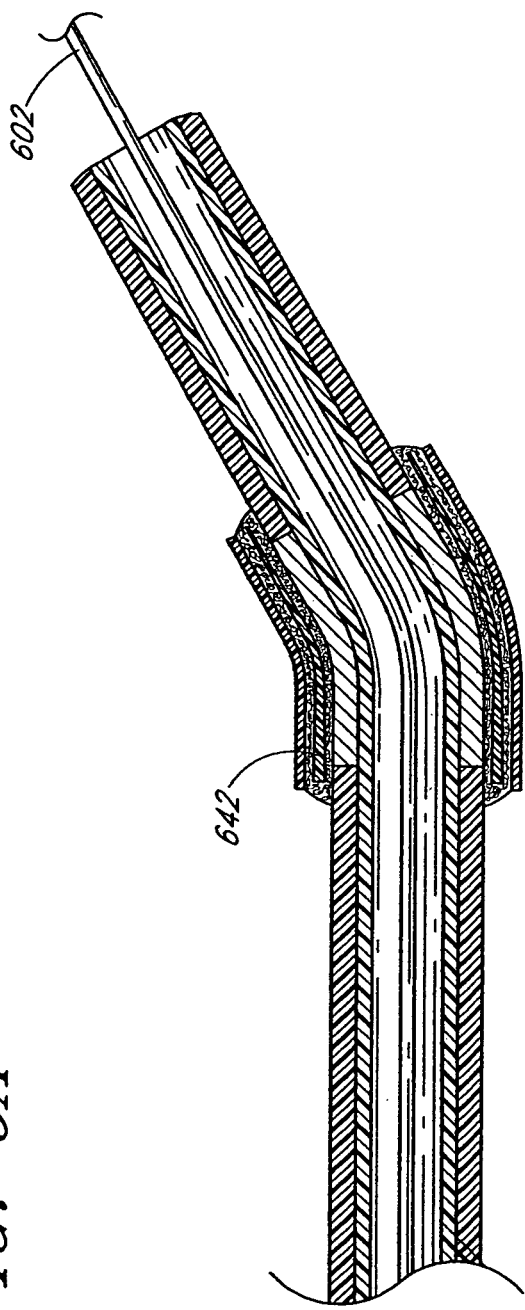
FIG. 6A
FIG. 6B

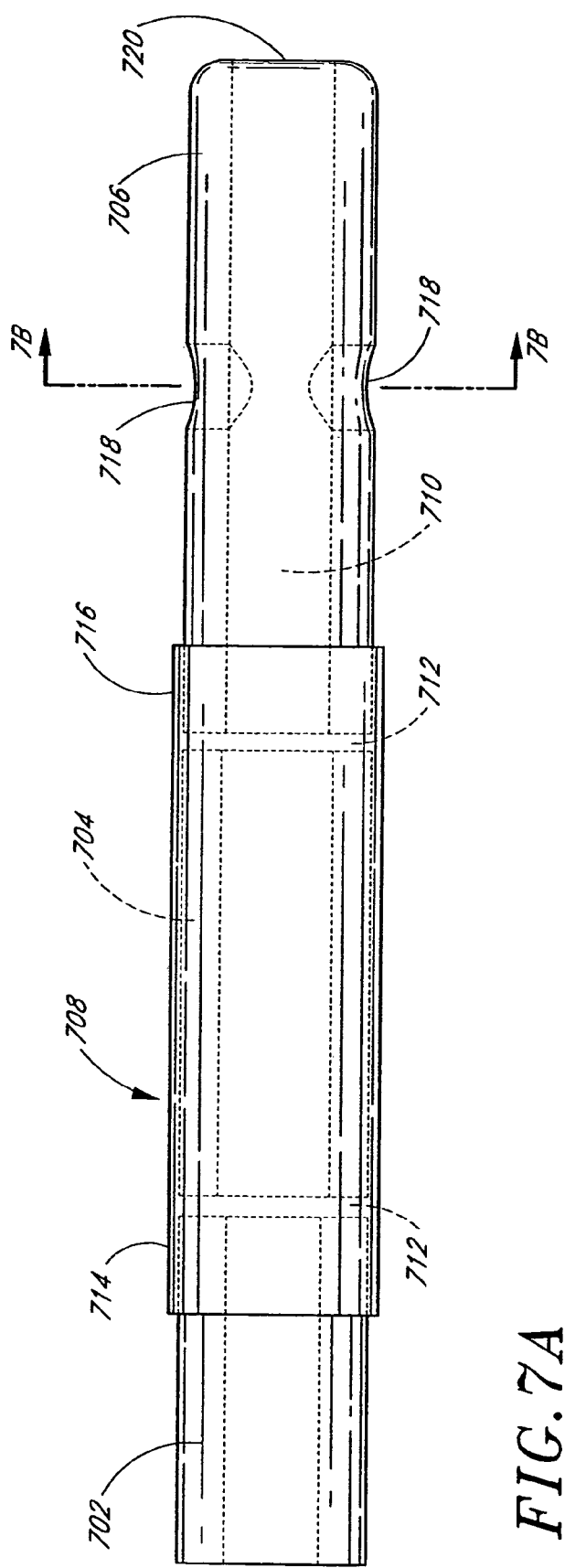
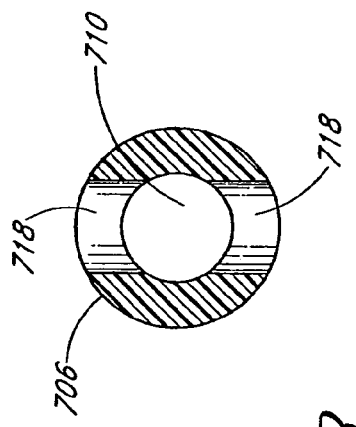
FIG. 7A
FIG. 7B

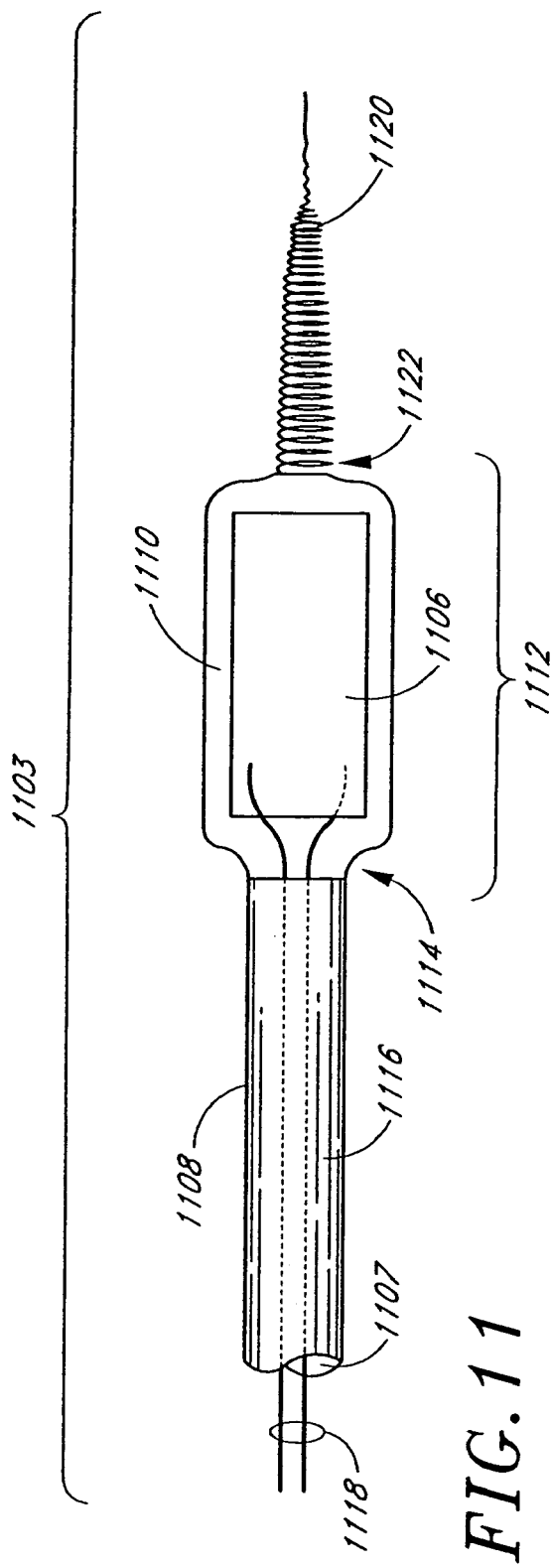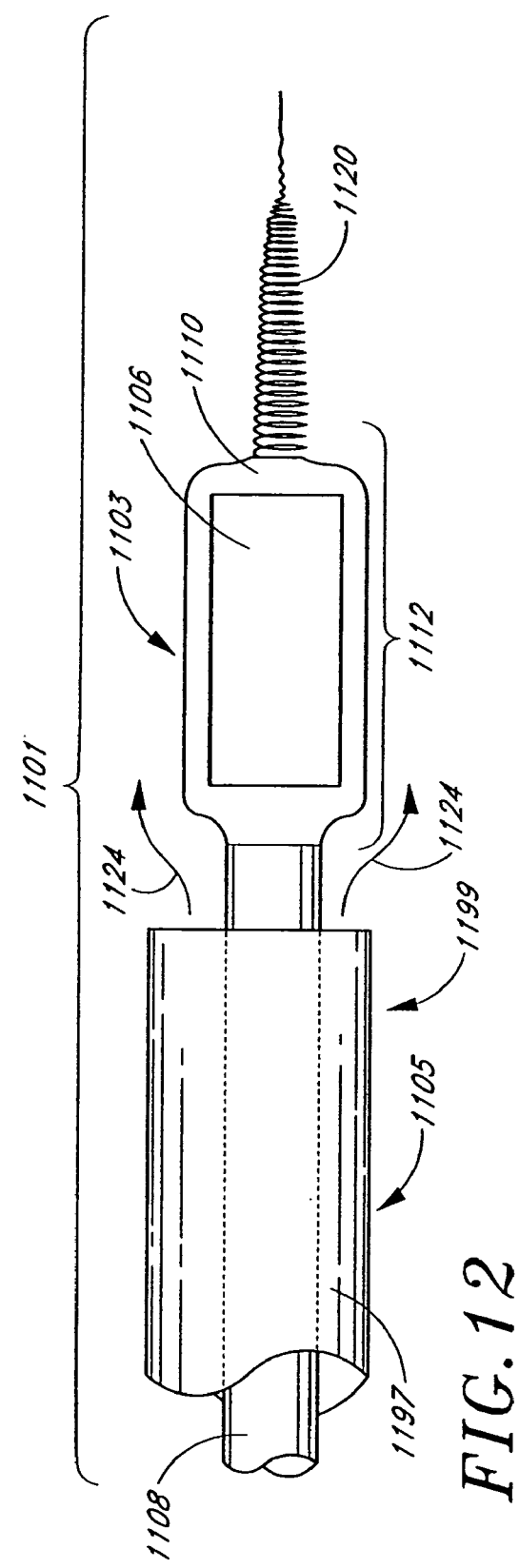
FIG. 11
FIG. 12

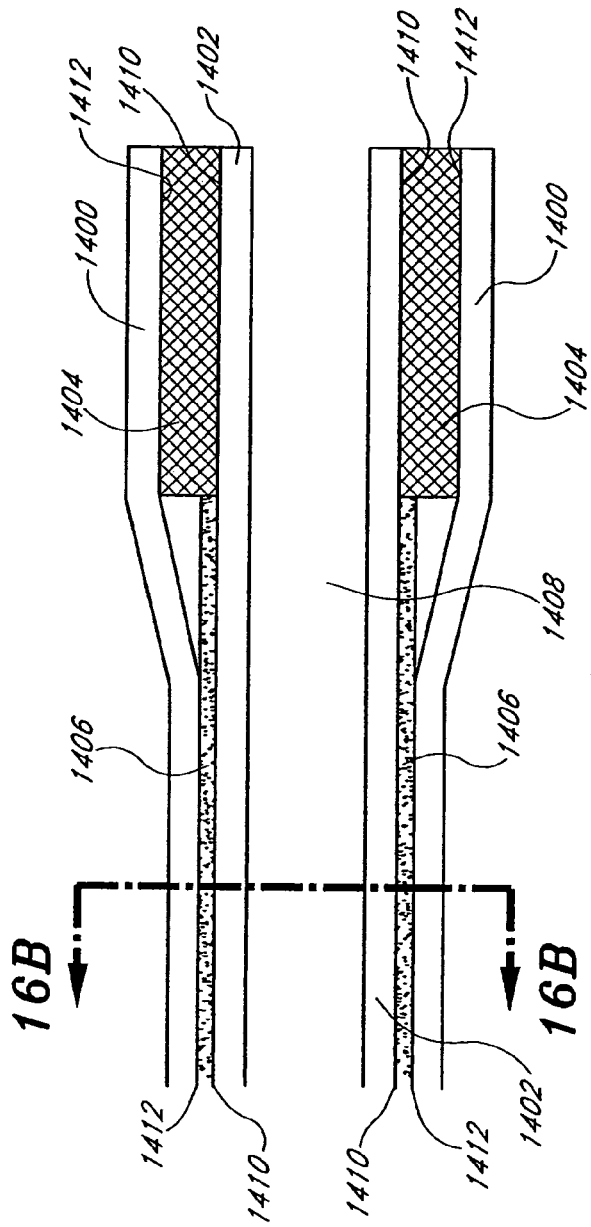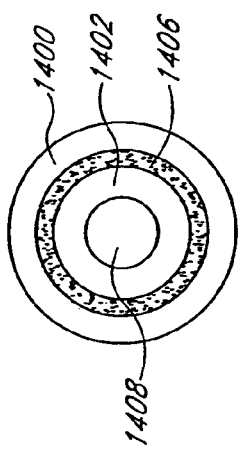
FIG. 16A
FIG. 16B

100 # METHOD OF MANUFACTURING ULTRASOUND CATHETERS

PRIORITY INFORMATION

This application is a divisional of U.S. patent Ser. No. 10/378,032, filed Feb. 28, 2003 now abandoned, which claims priority under 35 U.S.C. §119(e) from U.S. Provisional Patent Application Ser. No. 60/361,341, entitled "Small Vessel Catheter with Embedded Conductors" and filed Feb. 28, 2002 and is a continuation-in-part of U.S. patent application Ser. No. 10/309,417, entitled "Small Vessel Ultrasonic Catheter" and filed Dec. 3, 2002 now U.S. Pat No. 7,384,407, the entire contents of these applications are hereby incorporated by reference.

FIELD OF THE INVENTION

The present invention relates to a catheter having an ultrasound assembly useful for delivering ultrasound energy at a treatment site in a body. The apparatus is particularly well suited for delivering ultrasound energy at a treatment site located within a small blood vessel in the distal anatomy.

BACKGROUND OF THE INVENTION

Several therapeutic and diagnostic applications use ultrasound energy. For example, ultrasound energy can be used to enhance the delivery and therapeutic effect of various therapeutic compounds. See e.g., U.S. Pat. Nos. 4,821,740, 4,953, 565 and 5,007,438, the entire disclosure of which is hereby incorporated by reference herein. In some applications, it is desirable to use an ultrasound catheter to deliver the ultrasound energy and/or therapeutic compound to a specific treatment site in the body. Such an ultrasound catheter typically comprises an elongate member configured for advancement through a patient's vasculature. An ultrasound assembly is mounted along the distal end portion of the elongate member and is adapted for emitting ultrasound energy. The ultrasound catheter may include a delivery lumen for delivering the therapeutic compound to the treatment site. In this manner, the ultrasound energy can be emitted at the treatment site to enhance the desired therapeutic effects and/or delivery of the therapeutic compound.

In one particular application, ultrasound catheters have been successfully used to treat human blood vessels that have become occluded by plaque, thrombi, emboli or other substances that reduce the blood carrying capacity of the vessel. See e.g., U.S. Pat. No. 6,001,069, the entire disclosure of which is hereby incorporated by reference herein. To remove the blockage, the ultrasound catheter is advanced through the patient's vasculature to deliver solutions containing dissolution compounds directly to the blockage site. To enhance the therapeutic effects of the dissolution compound, ultrasound energy is emitted into the compound and/or the surrounding tissue.

In another application, ultrasound catheters may be used to perform gene therapy on an isolated region of a blood vessel or other body lumen. For example, as disclosed in U.S. Pat. No. 6,135,976, the entire disclosure of which is hereby incorporated by reference herein, an ultrasound catheter can be provided with one or more expandable members for occluding a section of the body lumen at a treatment site. A gene therapy composition is delivered to the treatment site through the delivery lumen of the catheter. The ultrasound assembly is used to emit ultrasound energy at the treatment site to enhance the entry of the gene composition into the cells in the body lumen.

In addition to the applications discussed above, ultrasound catheters may be used for a wide variety of other purposes, such as, for example, delivering and activating light activated drugs with ultrasound energy (see e.g., U.S. Pat. No. 6,176, 842, the entire disclosure of which is hereby incorporated by reference herein).

Over the years, numerous types of ultrasound catheters have been proposed for various therapeutic purposes. However, none of the existing ultrasound catheters is well adapted for effective use within small blood vessels in the distal anatomy. For example, in one primary shortcoming, the region of the catheter on which the ultrasound assembly is located (typically along the distal end portion) is relatively rigid and therefore lacks the flexibility necessary for navigation through difficult regions of the distal anatomy. Furthermore, it has been found that it is very difficult to manufacture an ultrasound catheter having a sufficiently small diameter for use in small vessels while providing adequate pushability and torqueability. Still further, it has been found that the distal tip of an ultrasound catheter can easily damage the fragile vessels of the distal anatomy during advancement through the patient's vasculature.

Accordingly, an urgent need exists for an improved ultrasound catheter that is capable of safely and effectively navigating small blood vessels. It is also desirable that such a device be capable of delivering adequate ultrasound energy to achieve the desired therapeutic purpose. It is also desirable that such a device be capable of accessing a treatment site in fragile distal vessels in a manner that is safe for the patient and that is not unduly cumbersome. The present invention addresses these needs.

SUMMARY OF THE INVENTION

In accordance with the foregoing, it is desired to provide an ultrasound catheter having increased flexibility and maneuverability. Such features are advantageous when a treatment is to be performed in the peripheral vasculature, and are especially advantageous when a treatment is to be performed in small vessels, such as in the neurovascular system.

As such, according to one embodiment of the present invention, an ultrasound catheter comprises an elongate tubular body. The elongate tubular body has a proximal region and a distal region opposite the proximal region. The tubular body defines a central lumen having a central lumen diameter. The ultrasound catheter further comprises an elongate, hollow inner core extending through the central lumen. The elongate, hollow inner core has an inner core outer diameter that is less than or equal to the central lumen diameter. The ultrasound catheter further comprises an ultrasound radiating member positioned within the distal region of the tubular body and between the tubular body and the inner core. The ultrasound catheter further comprises at least two electrical conductors extending between the tubular body proximal region and the tubular body distal region. The at least two electrical conductors are positioned between the tubular body and the inner core. The at least two electrical conductors are electrically connected to the ultrasound radiating member. The at least two electrical conductors are wrapped around the inner core a plurality of times in a region between the ultrasound radiating member and the tubular body proximal region.

According to another embodiment of the present invention, an ultrasound catheter comprises an elongate tubular body. The elongate tubular body has a proximal region and a distal region opposite the proximal region. The tubular body defines a central lumen having a central lumen diameter. The ultrasound catheter further comprises an elongate, hollow inner core extending through the central lumen. The elongate, hollow inner core has an inner core outer diameter that is less than or equal to the central lumen diameter. The ultrasound catheter further comprises an ultrasound radiating member positioned within the distal region of the tubular body and between the tubular body and the inner core. The ultrasound catheter further comprises at least two electrical conductors extending between the tubular body proximal region and the tubular body distal region. The at least two electrical conductors are positioned between the tubular body and the inner core. The at least two electrical conductors are electrically connected to the ultrasound radiating member. The at least two electrical conductors are disposed substantially parallel to a catheter axis in a region between the ultrasound radiating member and the tubular body proximal region.

According to another embodiment of the present invention, an apparatus comprises an elongate, hollow body. The elongate, hollow body has a proximal region, a distal region opposite the proximal region, a body thickness, and an inner lumen. The apparatus further comprises an ultrasound radiating member positioned within the body thickness of the elongate, hollow body. The apparatus further comprises a plurality of elongate electrical conductors extending between the elongate, hollow body proximal region and the ultrasound radiating member. The plurality of elongate electrical conductors are positioned within the body thickness of the elongate, hollow body.

BRIEF DESCRIPTION OF THE DRAWINGS

FIG. 2A is a cross-sectional view of a distal end of the ultrasound catheter of FIG. 1.

FIG. 2B is a cross-sectional view of the ultrasound catheter taken through line 2B-2B of FIG. 2A.

FIG. 6A is a cross-sectional view of the distal end of an ultrasound catheter including a bendable wire adapted for providing a shapeable tip.

FIG. 6B is a cross-sectional view of the embodiment of FIG. 6A with the shapeable tip pre-formed to facilitate advancement over a guidewire.

FIG. 7A is a top view of the distal end of an ultrasound catheter having a soft tip assembly.

FIG. 7B is a cross-sectional view of the soft tip assembly taken through line 7B-7B of FIG. 7A.

FIG. 11 is a side view of a distal end of a treatment wire wherein an ultrasound element is provided along the distal end of a hypotube.

FIG. 12 is a side view of a distal end of an ultrasound catheter that incorporates the treatment wire of FIG. 11.

FIG. 16A illustrates a longitudinal cross-sectional view of an ultrasound catheter having internal surfaces that are electrically conductive.

FIG. 16B illustrates a cross-sectional view of the ultrasound catheter of FIG. 16A taken along line 16B-16B.

DETAILED DESCRIPTION OF PREFERRED EMBODIMENTS

Figure 1:
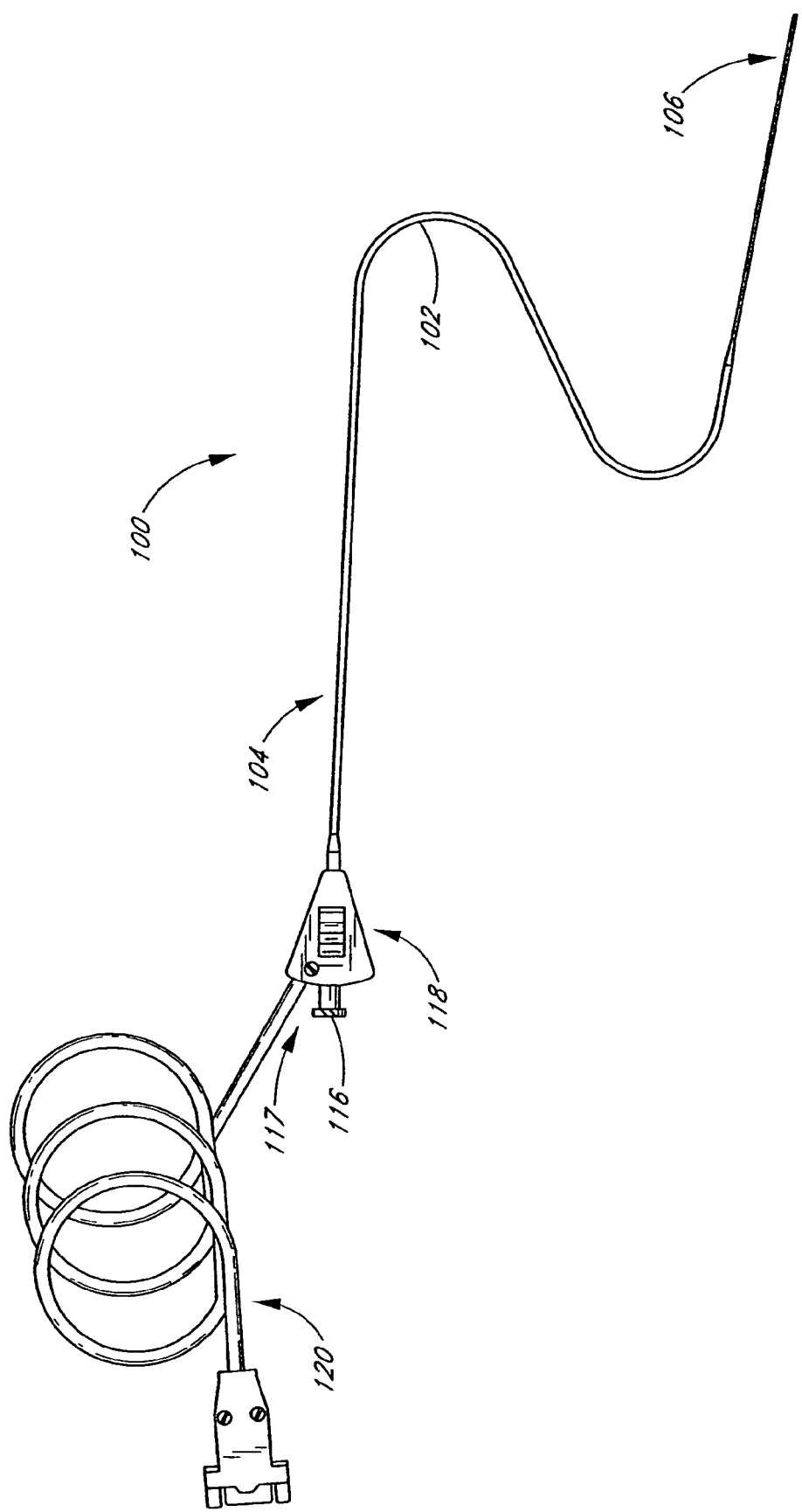
FIG. 1 is a side view of an ultrasound catheter that is particularly well suited for insertion into small blood vessels of the human body.

The advancement of an ultrasound catheter through a blood vessel to a treatment site can be difficult and dangerous, particularly when the treatment site is located within a small vessel in the distal region of a patient's-vasculature. To reach the treatment site, it is often necessary to navigate a tortuous path around difficult bends and turns. During advancement through the vasculature, bending resistance along the distal end portion of the catheter can severely limit the ability of the catheter to make the necessary turns. Moreover, as the catheter is advanced, the distal tip of the catheter is often in contact with the inner wall of the blood vessel. The stiffness and rigidity of the distal tip of the catheter may lead to significant trauma or damage to the tissue along the inner wall of the blood vessel. As a result, advancement of an ultrasound catheter through small blood vessels can be extremely hazardous. Therefore, a need exists for an improved ultrasound catheter design that allows a physician to more easily navigate difficult turns in small blood vessels while minimizing trauma and/or damage along the inner walls of the blood vessels.

To address this need, preferred embodiments of the present invention described herein provide an ultrasound catheter that is well suited for use in the treatment of small blood vessels or other body lumens having a small inner diameter. The ultrasound catheter can be used to enhance the therapeutic effects of drugs, medication and other pharmacological agents at a treatment site within the body. See e.g., U.S. Pat. Nos. 5,318,014, 5,362,309, 5,474,531, 5,628,728, 6,001,069, and 6,210,356. Certain preferred embodiments of the ultrasound catheter are particularly well suited for use in the treatment of thrombotic occlusions in small blood vessels, such as, for example, the cerebral arteries. In addition, preferred embodiments may also find utility in other therapeutic applications, such as, for example, performing gene therapy (see e.g., U.S. Pat. No. 6,135,976), activating light activated drugs for producing targeted tissue death (see e.g., U.S. Pat. No. 6,176,842) and causing cavitation to produce various desirable biological effects (see e.g., U.S. Pat. No. RE36,939). Moreover, such therapeutic applications may be used in wide variety of locations within the body, such as, for example, in other parts of the circulatory system, solid tissues, duct systems and body cavities. It is also anticipated that the ultrasound catheters disclosed herein, and variations thereof, may find utility in other medical applications, such as, for example, diagnostic and imaging applications.

Ultrasound catheters and methods disclosed herein, and similar variations thereof, may also be useful for applications wherein the ultrasound energy provides a therapeutic effect by itself. For example, ultrasound energy may be effective for uses such as preventing and/or reducing stenosis and/or restenosis, tissue ablation, abrasion or disruption, promoting temporary or permanent physiological changes in intracellular or intercellular structures, or rupturing micro-balloons or micro-bubbles for drug delivery. See e.g., U.S. Pat. Nos. 5,269,291 and 5,431,663. In addition, the methods and devices disclosed herein may also find utility in applications that do not require the use of a catheter. For example the methods and devices may be used for enhancing hyperthermic drug treatment or using an external ultrasound source to enhance the therapeutic effects of drugs, medication and other pharmacological agents at a specific site within the body or to provide a therapeutic or diagnostic effect by itself. See e.g., U.S. Pat. Nos. 4,821,740, 4,953,565, 5,007,438 and 6,096,000. The entire disclosure of each of the patents mentioned in this paragraph and the previous paragraph is hereby incorporated by reference herein and made a part of this specification.

As used herein, the term "ultrasound energy" is a broad term and is used in its ordinary sense and means, without limitation, mechanical energy transferred through pressure or compression waves with a frequency greater than about 20 KHz. In one embodiment, the waves of the ultrasound energy have a frequency between about 500 KHz and 20 MHz and in another embodiment between about 1 MHz and 3 MHz. In yet another embodiment, the waves of the ultrasound energy have a frequency of about 3 MHz.

As used herein, the term "catheter" is a broad term and is used in its ordinary sense and means, without limitation, an elongate flexible tube configured to be inserted into the body of a patient, such as, for example, a body cavity, duct or vessel.

Preferred Features of an Ultrasound Catheter

Referring now to FIGS. 1 through 2B, for purposes of illustration, preferred embodiments of the present invention provide an ultrasound catheter 100 that is particularly well suited for use within small vessels of the distal anatomy, such as, for example, in the remote, small diameter, neurovasculature in the brain.

As shown in FIG. 1 and 2A, the ultrasound catheter 100 generally comprises a multi-component tubular body 102 having a proximal end 104 and a distal end 106. The tubular body 102 and other components of the catheter 100 can be manufactured in accordance with any of a variety of techniques well know in the catheter manufacturing field. As discussed in more detail below, suitable material dimensions can be readily selected taking into account the natural and anatomical dimensions of the treatment site and of the desired percutaneous access site.

Preferably, the tubular body 102 can be divided into at least three sections of varying stiffness. The first section, which preferably includes the proximal end 104, is generally more stiff than a second section, which lies between the proximal end 104 and the distal end 106 of the catheter. This arrangement facilitates the movement and placement of the catheter 102 within small vessels. The third section, which includes ultrasound radiating element 124, is generally stiffer than the second section due to the presence of the ultrasound radiating element 124.

In each of the embodiments described herein, the assembled ultrasound catheter preferably has sufficient structural integrity, or "pushability," to permit the catheter to be advanced through a patient's vasculature to a treatment site without buckling or kinking. In addition, the catheter has the ability to transmit torque, such that the distal portion can be rotated into a desired orientation after insertion into a patient by applying torque to the proximal end.

The elongate flexible tubular body 102 comprises an outer sheath 108 (see FIG. 2A) that is positioned upon an inner core 110. In an embodiment particularly well suited for small vessels, the outer sheath 108 comprises extruded PEBAX, PTFE, PEEK, PE, polymides, braided polymides and/or other similar materials. The distal end portion of the outer sheath 108 is adapted for advancement through vessels having a very small diameter, such as those in the neurovasculature of the brain. Preferably, the distal end portion of the outer sheath 108 has an outer diameter between about 2 and 5 French. More preferably, the distal end portion of the outer sheath 108 has an outer diameter of about 2.8 French. In one preferred embodiment, the outer sheath 108 has an axial length of approximately 150 centimeters.

In other embodiments, the outer sheath 108 can be formed from a braided tubing formed of, by way of example, high or low density polyethylenes, urethanes, nylons, etc. Such an embodiment enhances the flexibility of the tubular body 102. For enhanced pushability and torqueability, the outer sheath 108 may be formed with a variable stiffness from the proximal to the distal end. To achieve this, a stiffening member may be included along the proximal end of the tubular body 102.

The inner core 110 defines, at least in part, a delivery lumen 112, which preferably extends longitudinally along the entire length of the catheter 100. The delivery lumen 112 has a distal exit port 114 and a proximal axis port 116. Referring again to FIG. 1, the proximal access port 116 is defined by drug inlet port 117 of a back end hub 118, which is attached to the proximal end 104 of the other sheath 108. The illustrated back end hub 118 is preferably attached to a control box connector 120, the utility of which will be described in more detail below.

The delivery lumen 112 is preferably configured to receive a guide wire (not shown). Preferably, the guidewire has a diameter of approximately 0.008 to 0.012 inches. More preferably, the guidewire has a diameter of about 0.010 inches. The inner core 110 is preferably formed from polymide or a similar material which, in some embodiments, can be braided to increase the flexibility of the tubular body 102.

With particular reference to FIGS. 2A and 2B, the distal end 106 of the catheter 102 preferably includes the ultrasound radiating element 124. In the illustrated embodiment, the ultrasound radiating element 124 comprises an ultrasound transducer, which converts, for example, electrical energy into ultrasound energy. In a modified embodiment, the ultrasound energy can be generated by an ultrasound transducer that is remote from the ultrasound radiating element 124 and the ultrasound energy can be transmitted via, for example, a wire to the ultrasound radiating element 124.

In the embodiment illustrated in FIGS. 2A and 2B, the ultrasound radiating element 124 is configured as a hollow cylinder. As such, the inner core 110 can extend through the lumen of the ultrasound radiating element 124. The ultrasound radiating element 124 can be secured to the inner core 110 in any suitable manner, such as with an adhesive. A potting material may also be used to further secure the mounting of the ultrasound radiating element along the central core.

In other embodiments, the ultrasound radiating element 124 can be configured with a different shape without departing from the scope of the invention. For example, the ultrasound radiating element may take the form of a solid rod, a disk, a solid rectangle or a thin block. Still further, the ultrasound radiating element 124 may comprise a plurality of smaller ultrasound radiating elements. The illustrated arrangement is the generally preferred configuration because it provides for enhanced cooling of the ultrasound radiating element 124. For example, in one preferred embodiment, a drug solution can be delivered through the delivery lumen 112. As the drug solution passes through the lumen of the ultrasound radiating element, the drug solution may advantageously provide a heat sink for removing excess heat generated by the ultrasound radiating element 124. In another embodiment, a return path can be formed in the space 138 between the outer sheath and the inner core such that coolant from a coolant system can be directed through the space 138.

The ultrasound radiating element 40 is preferably selected to produce ultrasound energy in a frequency range that is well suited for the particular application. Suitable frequencies of ultrasound energy for the applications described herein include, but are not limited to, from about 20 KHz to about 20 MHz. In one embodiment, the frequency is between about 500 KHz and 20 MHz and in another embodiment from about 1 MHz and about 3 MHz. In yet another embodiment, the ultrasound energy has a frequency of about 3 MHz.

As mentioned above, in the illustrated embodiment, ultrasound energy is generated from electrical power supplied to the ultrasound radiating element 124. The electrical power can be supplied through the controller box connector 120, which is connected to a pair wires 126, 128 that extend through the catheter body 102. The electrical wires 126, 128 can be secured to the inner core 110, lay along the inner core 110 and/or extend freely in the space between the inner core 110 and the outer sheath 108. In the illustrated arrangement, the first wire 126 is connected to the hollow center of the ultrasound radiating element 124 while the second wire 128 is connected to the outer periphery of the ultrasound radiating element 124. The ultrasound radiating element 124 is preferably, but is not limited to, a transducer formed of a piezolectic ceramic oscillator or a similar material.

With continued reference to FIGS. 2A and 2B, the distal end 104 of the catheter 100 preferably includes a sleeve 130, which is generally positioned about the ultrasound radiating element 124. The sleeve 130 is preferably constructed from a material that readily transmits ultrasound energy. Suitable materials for the sleeve 130 include, but are not limited to, polyolefins, polyimides, polyester and other materials having a relatively low impedance to ultrasound energy. Low ultrasound impedance materials are materials that readily transmit ultrasound energy with minimal absorption of the ultrasound energy. The proximal end of the sleeve 130 can be attached to the outer sheath 108 with an adhesive 132. To improve the bonding of the adhesive 132 to the outer sheath 108, a shoulder 127 or notch may be formed in the outer sheath for attachment of the adhesive thereto. Preferably, the outer sheath 108 and the sleeve 130 have substantially the same outer diameter.

In a similar manner, the distal end of the sleeve 130 can be attached to a tip 134. In the illustrated arrangement, the tip 134 is also attached to the distal end of the inner core 110. Preferably, the tip is between about 0.5 and 4.0 millimeters in length. More preferably, the tip is about 2.0 millimeters in length. As illustrated, the tip is preferably rounded in shape to reduce trauma or damage to tissue along the inner wall of a blood vessel or other body structure during advancement toward a treatment site.

With continued reference to FIG. 2B, the catheter 100 preferably includes at least one temperature sensor 136 along the distal end 106. The temperature sensor 136 is preferably located on or near the ultrasound radiating element 124. Suitable temperature sensors include but are not limited to, diodes, thermistors, thermocouples, resistance temperature detectors (RTDs), and fiber optic temperature sensors that used thermalchromic liquid crystals. The temperature sensor is preferably operatively connected to a control box (not shown) through a control wire, which extends through the catheter body 102 and back end hub 118 and is operatively connected to a control box through the control box connector 120. The control box preferably includes a feedback control system having the ability to monitor and control the power, voltage, current and phase supplied to the ultrasound radiating element. In this manner, the temperature along the relevant region of the catheter can be monitored and controlled for optimal performance. Details of the control box can be found in Assignee's co-pending provisional application entitled CONTROL POD FOR ULTRASONIC CATHETER, Application Ser. No. 60/336,630, filed Dec. 3, 2001, which is incorporated by reference in its entirety.

In one exemplary application of the ultrasound catheter 100 described above, the apparatus may be used to remove a thrombotic occlusion from a small blood vessel. In one preferred method of use, a free end of a guidewire is percutaneously inserted into the patient's vasculature at a suitable first puncture site. The guidewire is advanced through the vasculature toward a treatment site wherein the blood vessel is occluded by the thrombus. The guidewire wire is preferably then directed through the thrombus.

After advancing the guidewire to the treatment site, the catheter 100 is thereafter percutaneously inserted into the vasculature through the first puncture site and is advanced along the guidewire towards the treatment site using traditional over-the-guidewire techniques. The catheter 100 is advanced until the distal end 106 of the catheter 100 is positioned at or within the occlusion. The distal end 106 of the catheter 100 may include one or more radiopaque markers (not shown) to aid in positioning the distal end 106 within the treatment site.

After placing the catheter, the guidewire can then be withdrawn from the delivery lumen 112. A drug solution source (not shown), such as a syringe with a Luer fitting, is attached to the drug inlet port 117 and the controller box connector 120 is connected to the control box. As such, the drug solution can be delivered through the delivery lumen 112 and out the distal access port 114 to the thrombus. Suitable drug solutions for treating a thrombus include, but are not limited to, an aqueous solution containing Heparin, Uronkinase, Streptokinase, and/or tissue Plasminogen Activator (TPA).

The ultrasound radiating element 124 is activated to emit ultrasound energy from the distal end 106 of the catheter 100. As mentioned above, suitable frequencies for the ultrasound radiating element 124 include, but are not limited to, from about 20 KHz to about 20 MHz. In one embodiment, the frequency is between about 500 KHz and 20 MHz and in another embodiment between about 1 MHz and 3 MHz. In yet another embodiment, the ultrasound energy is emitted at a frequency of about 3 MHz. The drug solution and ultrasound energy are applied until the thrombus is partially or entirely dissolved. Once the thrombus has been dissolved to the desired degree, the catheter 100 is withdrawn from the treatment site.

Stiffening Component

Referring again to FIG. 2A, because the diameter of the distal exit port 114 is often relatively large compared with the diameter of the guidewire (not shown), a gap may exist between the inner rim of the tip 134 and the guidewire. If sufficiently large, this gap may cause the tip 134 of the catheter to catch or snag on an object along the exit port 114. If the tip 134 catches on an object, the exit port 114 may stretch (i.e., increase in diameter) as the catheter is pushed forward. This effect is particularly likely to occur at vessel bifurcations and will hereinafter be referred to as "fish-mouthing."

Figure 3:
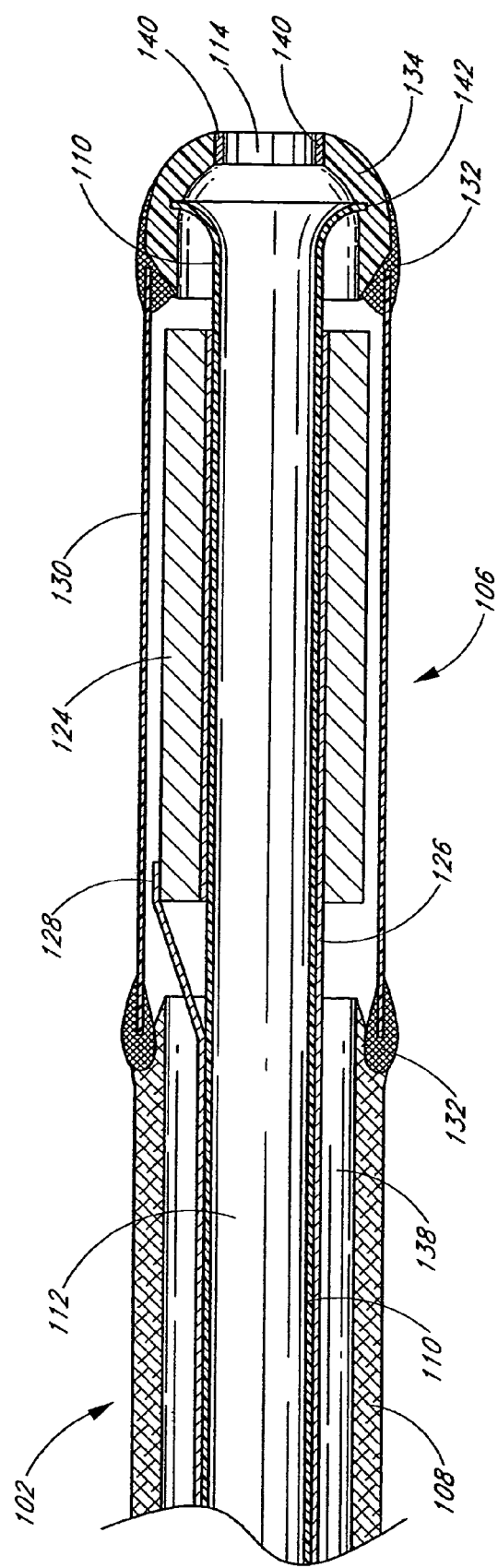
FIG. 3 is an alternative embodiment of the ultrasound catheter including a stiffener at the distal tip.

FIG. 3 illustrates an embodiment adapted to reduce the likelihood of fish-mouthing wherein a circular stiffening component 140 is provided along the distal tip 134. The circular stiffening component 140 reduces the gap between the tip 134 and the guidewire, and is preferably made of a stiff material, such as, for example, aluminum, that will prevent the tip 134 from fish-mouthing. Additionally, if the guidewire is formed with a variable diameter, cooperation of the guidewire and the circular stiffening component 140 may be advantageously used as a valve. By adjusting the relative positions of the guidewire and catheter, it is possible to control the delivery of drugs, medications, or other therapeutic compounds through the exit port 114 along the tip 134. As seen in FIG. 3, this embodiment also includes a variation of the inner core 110A having a flared end that may be inserted into a circumferential notch 142 formed in the distal tip 134. Insertion of the flared end into the circumferential notch provides for enhanced structural integrity.

In alternative embodiments, fish-mouthing may be prevented by increasing the thickness of the tip 134, or by manufacturing the tip 134 using a material with increased stiffness. In such embodiments, the tip 134 will have decreased flexibility, and therefore will be less susceptible to fish-mouthing.

Flexible Joint

Referring again to FIG. 2A, in modified embodiments of the present invention, the rigidity of the catheter along the joint (hereinafter referred to as the "proximal element joint") between the outer sheath 108 and sleeve 130 may be reduced significantly. The rigidity of the proximal element joint is reduced to further enhance flexibility, prevent kinking of the flexible support section of the catheter, and to facilitate tracking of the catheter over the guidewire.

In such embodiments, the used of an adhesive may be eliminated, and the proximal end of the sleeve 130 may be attached to the outer sheath 108 at the proximal element joint using a direct bonding method adapted to create a more flexible proximal element joint. Examples of such direct bonding methods include, but are not limited to, the use of heat, a solvent, a mold, or a cast. Alternatively, a reflow, or "die wiping" technique may be employed wherein an extruded catheter shaft is covered with a heat shrink tube and heated to reflow and bond the polymers within the catheter shaft. An external heat source may be employed in a reflow technique, or if the catheter includes metal components at the proximal element joint, radio frequency ("RF") energy may be used to heat and bond the polymers within the catheter shaft.

Figure 4:
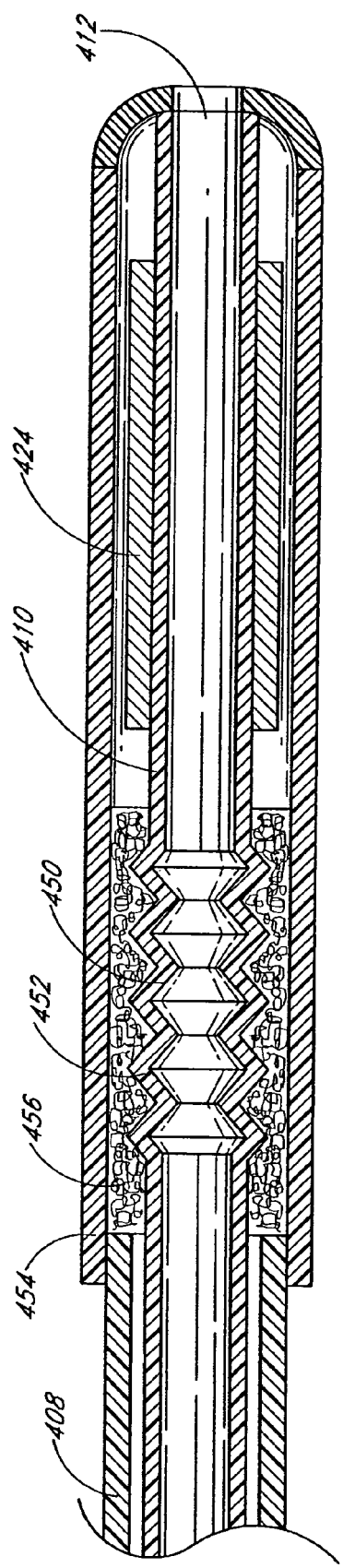
FIG. 4 is a cross-sectional view of the distal end of an ultrasound catheter wherein a portion of the inner core has a corrugated configuration for enhanced flexibility.

FIG. 4 illustrates yet another alternative embodiment for reducing the rigidity of the proximal element joint to thereby enhance the flexibility of the ultrasound catheter. As illustrated in FIG. 4, the inner core 410 includes a corrugated portion 452 along the proximal element joint just proximal of the ultrasound radiating element 424. In such embodiments, a Teflon® liner 450 may be adapted to surround the inner surface of the corrugated portion 452 of the inner core 410 to prevent the guidewire from catching on the corrugations. Additionally, a flexible filler material 456 and a flexible cover sleeve 454 may be adapted to cover the exterior surface of the corrugated portion 452 of the catheter to prevent the catheter from catching on the interior walls of the vessel anatomy. A corrugated portion 452 of the inner core 410 may be created by placing a close-fitting pin within a portion of the polyimide material used to form the inner core, and applying a compressive force to the polyimide material on either side of the pin. When the pin is removed from the inner core 410, the corrugated portion 452 of the inner core 410 will have enhanced flexibility and will thereby increase the flexibility of the ultrasound catheter.

In still other embodiments, the rigidity of the proximal element joint may be further reduced by forming the inner core 410 of the delivery lumen 412 of a material with increased flexibility and resistance to kinking. For example, the inner core 410 of the delivery lumen 412 may comprise a Teflon®-lined polyimide shaft. Additionally, a coil or braid may be incorporated into the delivery lumen 412, thereby further reducing susceptibility to kinking without increasing the rigidity of the catheter.

Figure 5:
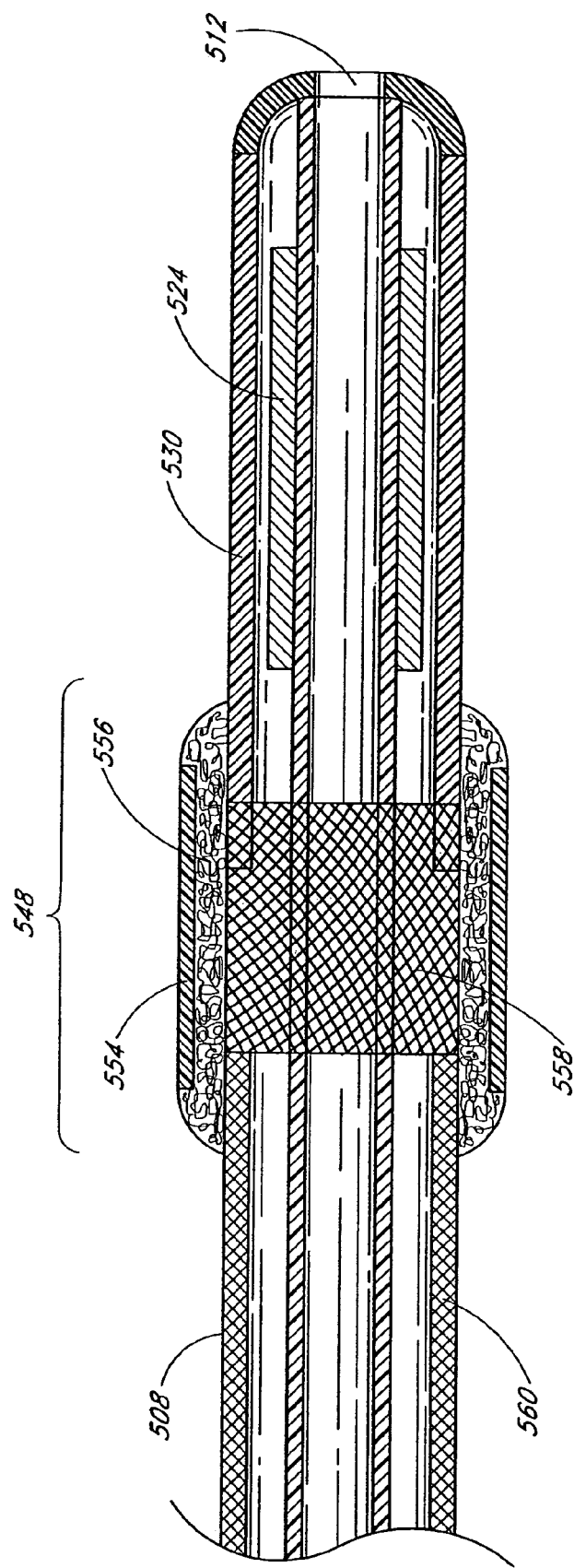
FIG. 5 is a cross-sectional view of the distal end of an ultrasound catheter wherein the proximal joint comprises braided sections for enhanced flexibility.

FIG. 5 illustrates yet another alternative embodiment wherein the rigidity of the proximal element joint 548 is reduced by providing a outer sheath 508 that includes an embedded braid 560. Furthermore, the outer sheath 508 is attached to the sleeve 530 using a flexible exposed braided portion 558. A flexible filler material 556 and a flexible cover sleeve 554 are used to bond the outer sheath 508, the sleeve 530 and the exposed braided portion 558 together. This embodiment provides the catheter with a flexible region just proximal to the ultrasound radiating member 524. In various preferred embodiments, the braided sections may be formed of high or low density polyethylenes, urethanes or nylons.

Sharpeable Tip

FIG. 6A illustrates yet another modified embodiment wherein the ultrasound catheter provides improved tracking over the guidewire 602. Prolapsing of a guidewire is most likely to occur at small vessel radii, where the guidewire 602 follows a sharp turn, and where the angle θ formed by the intersection between the guidewire 602 and the catheter body is large. In order to reduce the incident angle θ between the guidewire and catheter body, a tapered wire 642 is provided along the exterior of the outer sheath 608 for shaping the distal end of the catheter. The tapered wire 642 may be set in a flexible potting or filler material 644, which is contained within a flexible sleeve 646. The tapered wire 642 is preferably comprised of a pliable material, such that it may be pre-formed into a selectable desired orientation before use. Pre-forming of the tapered wire 642 assists the physician in steering the catheter to follow the guidewire 602 reliably around small vessel radii by reducing the angle θ formed by the intersection between the guidewire 602 and the catheter body. The tapered wire is preferably provided in the region surrounding the ultrasound radiating element 624. FIG. 6B illustrates the embodiment of FIG. 6A in use with the tip pre-formed for improved tracking over the guidewire.

Soft Tip Assembly

In addition to having excellent flexibility, it is also desirable for an ultrasound catheter to have a rounded and/or soft tip assembly for minimizing trauma or damage to the tissue along the inner wall of the blood vessel. This feature is particularly important during advancement through small blood vessels in the neurovasculature.

FIG. 7A illustrates an alternative embodiment wherein the distal end portion of an ultrasound catheter is provided with a soft tip assembly 700. In the illustrated embodiment, the ultrasound catheter generally comprises an elongate shaft body 702, an ultrasound radiating element 704, an elongate soft tip 706 and a connecting sleeve 708. The soft tip 706 of the catheter is constructed to be softer and more flexible than the shaft body 702 for the purpose of minimizing or eliminating damage to the tissue along the inner wall of a blood vessel. In the illustrated embodiment, the soft tip 706 is configured as a substantially hollow member including a delivery lumen 710. The lumen 710 may be used for receiving a guidewire and/or for delivering drugs to a treatment site. Preferably, the shaft body 702 and the soft tip 706 have substantially the same outer diameter. The delivery lumen 710 terminates at an exit port 720 at the extreme distal tip of the soft tip assembly.

Still referring to FIG. 7A, the ultrasound radiating element 704 is provided at a location just distal to the shaft body 702 and just proximal of the soft tip 710. Preferably, a small gap 712 is provided between the ultrasound radiating element 704 and the elongate body 702 and also between the ultrasound radiating element 704 and the soft tip 706. In the illustrated embodiment, a single cylindrical ultrasound radiating element 704 is provided, however, in alternative embodiments, others variations may be used, such as, for example a plurality of smaller ultrasound radiating elements.

In the illustrated embodiment, the shaft body 702, ultrasound radiating element 704 and soft tip 706 are secured together by the sleeve 708. The ultrasound radiating element 704 is contained within the lumen of the sleeve 708. The proximal end 714 of the sleeve 708 extends over the distal portion of the shaft body 702. The distal end 716 of the sleeve 708 extends over the proximal end of the soft tip 706. In one embodiment, the sleeve 708 is formed of heat shrink tubing. To maximize effectiveness of the ultrasound catheter, the sleeve 708 is preferably constructed of a material having a low impedance to ultrasound energy. FIG. 7B illustrates a cross-sectional view of the soft tip assembly of FIG. 7A as seen through line 7B-7B.

Referring again to FIG. 7A, the illustrated embodiment of the soft tip assembly 706 is formed with a plurality of side holes 718. The side holes 718 are in communication with the delivery lumen 710 and are provided for enhancing the delivery of drugs to the treatment site. Using the side holes 718, the therapeutic agent can be delivered radially at a location closer to the ultrasound radiating element 704. The illustrated embodiment includes two side holes, however, in alternative embodiments, any number of side holes may be used without departing form the spirit and scope of the invention. Alternatively, the soft tip assembly may be configured without any side holes.

In alternative embodiments, the soft tip assembly may have a solid tip wherein drugs exit the tip assembly only through side ports. In the embodiments with a solid tip, the guidewire exits the catheter through a side port, such as in a rapid exchange or monorail catheter design. In another embodiment, the soft tip assembly includes a radiopaque material to provide for high visibility under fluoroscopy. In various alternative embodiments, the soft tip assembly may have a variety of different lengths, such as, for example, 1 mm, 3 mm and 6 mm.

In operation, the ultrasound catheter is advanced over a guidewire that extends through the delivery lumen 710. As the ultrasound catheter is advanced through a small blood vessel, the soft tip assembly bends and conforms to the shape of the blood vessel to reduce the pressure applied along the inner wall. The rounded tip of the soft tip assembly also minimizes trauma to the tissue as it is advanced along the inner walls of the blood vessels. The soft tip assembly can bend to facilitate the advancement of the catheter, yet will return to substantially its original shape. After the ultrasound element is positioned in the desired location, the guidewire may be removed and the delivery lumen 710 used for the delivery of a therapeutic agent to the treatment site.

The soft tip assembly is preferably made of a soft polymer extrusion, such as, for example, polyimide. In one preferred method of construction, the soft tip assembly is constructed by first cutting the extruded soft tubular body into a length of approximately 3 to 6 mm. The distal tip is then rounded and smoothed using a heated die with the desired contour. In the embodiments wherein side holes are provided, the side holes are created using a 0.010 inch hole plunger. The soft tip assembly is then attached to the elongate shaft body using an adhesive or by thermal bonding. Alternatively, a length of heat shrink tubing may be used to secure the shaft body to the soft tip assembly.

Ultrasound Element on a Guidewire

Figures 8, 9, 10:
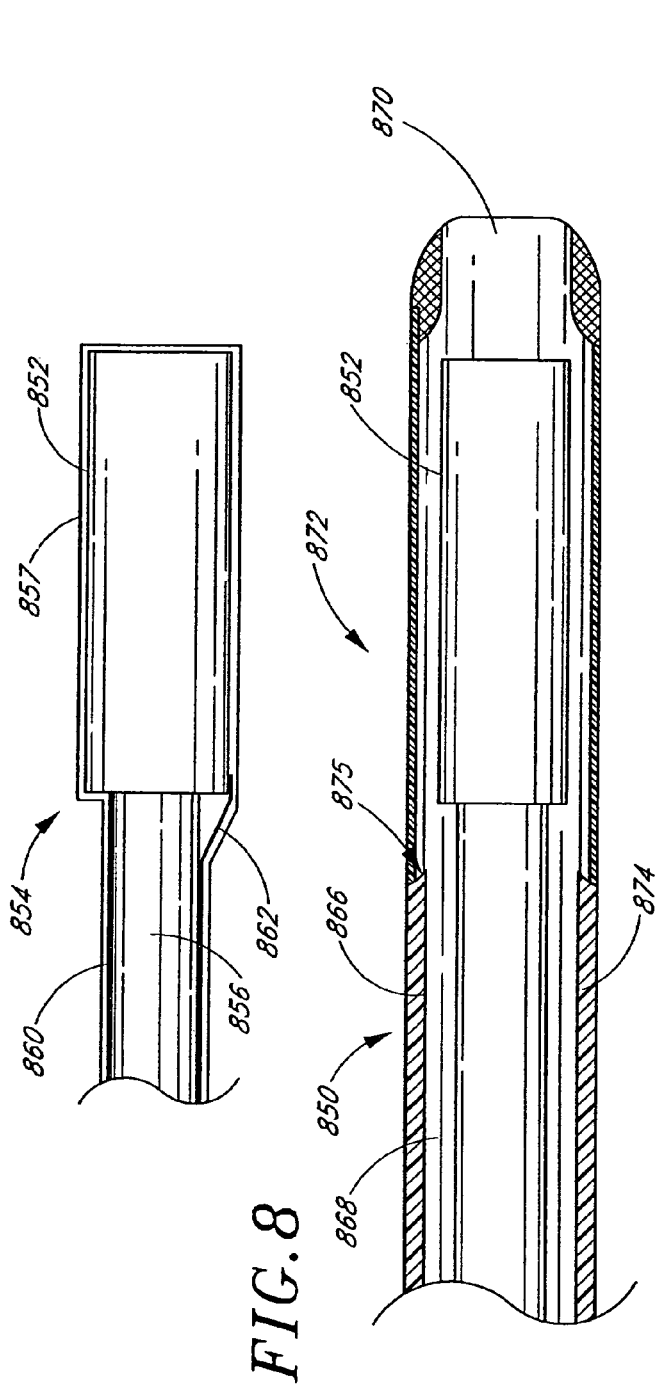
FIG. 8 is a side view an ultrasound element attached to the distal end of a guidewire.
FIG. 9 is a cross-sectional view of an ultrasound catheter used with the ultrasound element and guidewire of FIG. 8.
FIG. 10 is a cross-sectional view of a distal end of another modified embodiment of an ultrasound catheter that can be used with the ultrasound element and guidewire of FIG. 8.

FIGS. 8 and 9 illustrate another modified embodiment of an ultrasound catheter 850. As shown in FIG. 8, in this embodiment, an ultrasound radiating element 852 is connected to or mounted on a distal end 854 of a guidewire 856. In the illustrated arrangement, the ultrasound radiating element 852 is in the shape of a hollow cylinder. As such, the guidewire 856 can extend through the ultrasound radiating element 852, which is positioned over the guidewire 856. The ultrasound radiating element 852 can be secured to the guidewire 856 in any suitable manner, such as with an adhesive. In other embodiments, the ultrasound radiating element 856 can be of a different shape, such as, for example, a solid cylinder, a disk, a solid rectangle or a plate attached to the guidewire 856. The ultrasound radiating element 852 can also be formed from a plurality of smaller ultrasound elements.

In the illustrated embodiment, ultrasound energy is generated from electrical power supplied to the ultrasound radiating element 852. As such, the ultrasound radiating element 852 is connected to a pair of wires 860, 862 that can extend through the catheter body. In the illustrated embodiment, the wires 860, 862 are preferably secured to the guidewire 856 with the first wire 860 is connected to the hollow center of the ultrasound radiating element 852 and the second wire 862 connected to the outer periphery of the ultrasound radiating element 852. As with the previous embodiments, the ultrasound radiating element 852 is preferably formed from, but is not limited to, a piezolectic ceramic oscillator or a similar material. Other wiring schemes include wires connected to both ends of a solid transducer or both sides of a block. The ultrasound radiating element 852 and the wires 860, 862 are preferably covered with a thin insulating material 857.

FIG. 9 illustrates one embodiment of a catheter 850 that can be used with the guidewire 856 described above. In this embodiment, the catheter 850 includes an outer sheath 866, which defines the delivery lumen 868. As such, the illustrated embodiment does not include an inner core. The delivery lumen 868 includes a distal opening 870. As will be explained below, in one arrangement, the distal opening 870 can be configured such that the guidewire 856 and the ultrasound radiating element 852 can be withdrawn into the catheter 850 through the distal opening 870. In such an arrangement, a distal end 872 of the catheter 850 preferably includes a sleeve 874, that is constructed from a material that readily transmits ultrasound energy as described above. In another arrangement, the distal opening 870 can be configured such that ultrasound radiating element 852 can not be withdrawn into the catheter 850 through the distal opening 870. In such an arrangement, the ultrasound radiating element 852 is configured to operate outside the catheter 850 near the distal opening 870.

In one embodiment, the distal end 854 of the guidewire 856 is percutaneously inserted into the arterial system at a suitable first puncture site. The guidewire 856 and the ultrasound radiating element 852 are advanced through the vessels towards a treatment site, which includes a thrombotic occlusion. The guidewire 856 is preferably then directed through the thrombotic occlusion.

The catheter 850 is thereafter percutaneously inserted into the first puncture site and advanced along the guidewire 856 towards the treatment site using traditional over-the-guidewire techniques. The catheter 850 is advanced until the distal end of the catheter 856 is positioned at or within the occlusion. Preferably, the distal end includes radio opaque markers to aid positioning the distal end within the treatment site.

In one embodiment, the guidewire 856 can then be withdrawn until the ultrasound radiating element 852 is positioned within the distal end 874 of the catheter 850. In such an arrangement, the catheter 850 can include a proximal stop 875 to aid the positioning of the ultrasound radiating element 852. In another embodiment, the guidewire can be withdrawn until the ultrasound radiating element 852 is located near or adjacent the distal opening 870. The catheter 850 can then be operated as described above.

In another modified embodiment, a standard guidewire (not shown) is percutaneously inserted into the first puncture site and advanced through the vessels towards and preferably through the occlusion. The catheter 850 is thereafter percutaneously inserted into the first puncture site and advanced along the standard guidewire towards the treatment site using traditional over-the-guidewire techniques. The catheter 850 preferably is advanced until the distal end of the catheter 850 is positioned at or within the occlusion. The standard guidewire can then be withdrawn from the delivery lumen. The guidewire 856 and ultrasound radiating element 852 of FIG. 8 can then be inserted into the delivery lumen. In one embodiment, the ultrasound radiating element 852 is advanced until it is positioned in the distal end of the catheter 850. In another embodiment, the ultrasound radiating element 852 is advanced until it exits the distal end 870 of the delivery lumen 868. The catheter can then be operated as describe above.

FIG. 10 illustrates yet another modified embodiment of an ultrasound catheter 1000 that can be used with the guidewire 1056 and ultrasound radiating element 1052, as described above. In this embodiment, the guidewire lumen 1068 is defined by an inner sleeve or tube 1002. The distal end 1070 of the delivery lumen 1068 can be configured as described above for preventing or withdrawing the ultrasound radiating element 1052 into catheter 1050. In the illustrated arrangement, the delivery lumen 1068 can be used to transport the drug solution. In another arrangement, the space 1004 between the inner core 1002 and the outer sheath 1066 can be used to transport the drug solution. In such an arrangement, the outer sheath 1066 preferably includes one or more holes positioned at the distal end 1072 of the outer sheath 1066. The catheter can be advanced on the guidewire 856 of FIG. 8 or a standard guidewire as described above.

Ultrasound Element on a Hypotube

FIGS. 11 and 12 illustrate yet another embodiment of an ultrasound catheter 1101 that is particularly well suited for use with small vessels of the distal anatomy. As shown in FIG. 12, this embodiment of the ultrasound catheter 1101 generally comprises a treatment wire 1103 and a microcatheter 1105.

FIG. 11 illustrates a preferred embodiment of a treatment wire 1103. As shown in FIG. 11, in this embodiment, an ultrasound radiating element 1106 is connected to the distal tip of a hypotube 1108. As discussed with reference to the small vessel catheters described above, the ultrasound radiating element can take many shapes and forms. The ultrasound radiating element 1106 is potted in an insulating material either as a conformal coating or potted inside an outer sleeve. The potting 1110 over the ultrasound radiating element 1106 sections is optimized for transmission of ultrasound energy. In the embodiment illustrated in FIG. 11, the width of the potted ultrasound radiating element 1112 is approximately 0.018 inches. An epoxy or similar adhesive known in the catheter manufacturing field connects the potted ultrasound radiating element 1112 with the hypotube 1108 at junction 1114.

The hypotube 1108 is made from Nitinol or stainless steel or other suitable material in accordance with the techniques and materials known in the catheter manufacturing field. In one embodiment, the hypotube has a diameter of approximately 0.014 to 0.015 inches. The hypotube 1108 provides an insulated lumen 1116 through which one can run power wires 1118 for the ultrasound radiating element 1106 or wires for temperature sensors (not shown) in the microcatheter 1105. The microcatheter 1105, into which the treatment wire 1103 is inserted, has a diameter greater than the width of the potted ultrasound radiating element 1112.

As shown in FIG. 11, in this embodiment, a flexible nose 1120 is connected to the distal end of the potted ultrasound radiating element 1112. An epoxy or similar adhesive known in the catheter manufacturing field connects the flexible nose 1120 to the potted ultrasound radiating element 1112 at junction 1122. The flexible nose 1120 is at least approximately 3 millimeters in length and functions as a guidewire when the treatment wire 1103 is inserted into a microcatheter 1105. In the embodiment illustrated in FIG. 11, the flexible nose 1120 is a soft coil made of metal or another suitable material known in the art. The flexible nose 1120 facilitates the delivery of the potted ultrasound radiating element 1112 through the microcatheter 1105 and into the vessel lumen of the treatment site. Preferably, the flexible nose 1120 is tapered in a manner so that the distal end of the nose has a smaller diameter than the proximal end.

In use, a free end of a guidewire is percutaneously inserted into the arterial system at a suitable first puncture site. The guidewire is advanced through the vessels toward a treatment site, such as, for example, a thrombotic occlusion in the middle cerebral artery.

The microcatheter 1105 is thereafter percutaneously inserted into the first puncture site and advanced along the guidewire towards the treatment site using traditional over-the-guidewire techniques. The catheter 1105 is advanced until the distal end 1199 of the catheter 1105 is positioned at or within the occlusion. Preferably, the distal end 1199 includes radio opaque markers to aid positioning the distal end 1199 within the treatment site.

The guidewire can then be withdrawn from the delivery lumen 1197 of the microcatheter 1105. As illustrated in FIG. 12, the treatment wire 1103 is then inserted and advanced through the microcatheter 1105 to the treatment site. The potted ultrasound radiating element 1112 of the treatment wire 1103 is advanced beyond the distal end 1199 of the microcatheter and into lumen of the vessel. Once at the target site, the ultrasound radiating element 1106 provides ultrasound energy.

Preferably, drugs 1124, including but not limited to drugs having thrombolytic effects, are infused through the microcatheter 1105 and delivered into the vessel around the ultrasound radiating element 1106 at the same time the ultrasound radiating element 1106 emits energy. It is believed that the transmission of ultrasound energy at the treatment site enhances drug uptake and activity and has other therapeutic effects. Preferably, the potted ultrasound radiating element 1112 extends far enough away from the distal tip 1199 of the microcatheter 1105 to facilitate the infusion of drugs (shown by arrow 1124) through the microcatheter 1105 and into the vessel.

Overview of Ultrasound Catheter with Embedded Conductors

In certain embodiments, wherein an ultrasound radiating member is positioned between an inner elongate tubular body and an outer elongate tubular body, it is desired to pass elongate electrical conductors to the ultrasound radiating member from the proximal end of the catheter, thereby allowing an externally-generated driving signal to be provided to the ultrasound radiating member. In addition, in embodiments wherein a temperature sensor is positioned in the distal region of the catheter, it is desired to pass one or more elongate electrical conductors to the temperature sensor from the proximal end of the catheter, thereby allowing a distal temperature signal to be monitored at the proximal end of the catheter. The configuration of such elongate electrical conductors can be manipulated to affect the stiffness, torqueability, pushability, flexibility and other mechanical parameters of the catheter, thereby affecting accessibility of remote targets in the patient's vasculature.

Such embedded conductor configurations are discussed in greater detail in this section. These embodiments are particularly well-suited for use with small vessels of the distal anatomy, such as, for example, the vessels of the neurovascular system. However, such embodiments are also well-suited for the treatment of long segment peripheral arterial occlusions.

Figure 13A:
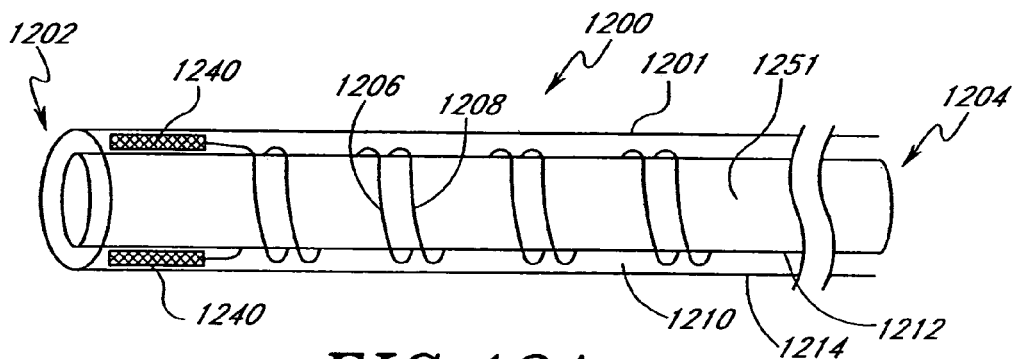
FIG. 13A is a partial cutaway view of one embodiment of an ultrasound catheter with embedded conductive wires that are spirally wrapped parallel to each other.

Referring now to FIG. 13A, an ultrasonic catheter 1200 generally comprises a multi-component tubular body 1201 having a proximal end 1204 and a distal end 1202. The tubular body 1201 and other components of the catheter 1200 can be manufactured in accordance with any of a variety of techniques well known in the catheter manufacturing field, and as explained above.

The ultrasonic catheter 1200 also comprises one or more ultrasound radiating members 1240 at its distal end 1202. Suitable material dimensions for the ultrasound radiating member 1240 can be readily selected taking into account the natural and anatomical dimensions of the treatment site and of the desired percutaneous access site, as explained above. In other embodiments, the ultrasonic catheter 1200 further comprises a temperature sensor (not shown) positioned within the catheter distal region, as described above. In one preferred embodiment of an ultrasonic catheter 1200, a central lumen 1251 can be concentrically placed over a guidewire (not shown) which has been previously navigated to the target area under, for example, fluoroscopic localization by a skilled surgeon or medical practitioner.

The ultrasonic catheter 1200 generally comprises one or more electrically conductive wires or fibers 1206, 1208 that extend along the length of the catheter 1200. In certain embodiments, the conductive wires 1206, 1208 generally reside within the wall 1210 of the tubular body 1201. In such embodiments, the wall 1210 of the tubular body 1201 comprises an inner portion 1212 and an outer portion 1214. In such embodiments, the conductive wires 1206, 1208 can be located in between the inner portion 1212 and outer portion 1214 of the wall 1210.

The inner portion 1212 provides a barrier against the contents of the central lumen 1251, such as, for example, therapeutic drugs infused through the central lumen 1251 and out the distal end 1202 of the catheter to a treatment site within the patient's vasculature. The outer portion 1214 provides a barrier against the environment in which the catheter 1200 resides, which may include, for example, blood or other bodily fluids.

The inner portion 1212 and outer portion 1214 of the wall 1210, and the wall 1210 in general, with the exception of the conductive wires 1206, 1208 embedded in the wall 1210, is made of insulating material, such as, for example, polyimide, high or low density polyethylenes, urethanes, nylons, and the like. Consequently, the conductive wires 1206, 1208 are electrically isolated from the central lumen 1251 and the environment in which the catheter 1200 resides.

The conductive wires 1206, 1208 are also preferably electrically isolated from each other. In one embodiment, the wires 1206, 1208 are arranged and configured in a manner to prevent contact between them. For example, the wires 1206, 1208 may be arranged along and/or around the central lumen in a manner which prevents any contact between the wires 1206, 1208. Also, electrically insulating material may placed between the wires 1206, 1208 to prevent contact between them. In another embodiment, the wires 1206, 1208 are covered with insulating coating material either in addition to or in lieu of placing insulating material between the wires 1206, 1208 or making the wall 1210 from insulating material.

The physical configuration or layout of the conductive wires 1206 and 1208 embedded within the wall 1210 of the tubular body 1201 can be adjusted to determine the mechanical attributes of the catheter 1200. The conductive wires 1206, 1208 may be arranged in various architectures such as, for example, linear arrays, weaving, spiraling, and other patterns which modulate stiffness, torquability, pushability, flexibility and other mechanical parameters of the catheter which relate to accessibility of remote targets.

Figure 13B:
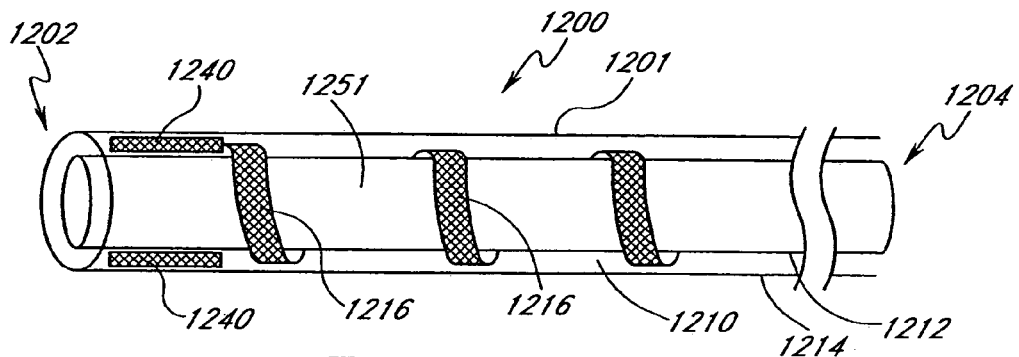
FIG. 13B is a partial cutaway view of one embodiment of an ultrasound catheter with embedded conductive wires that are spirally wrapped into a unitary cable.

In one embodiment, shown in FIG. 13A, both conductive wires 1206, 1208 spiral around the central lumen 1251 and remain substantially parallel to each other at all times along the length of the catheter 1200. In a modified embodiment, the wires 1206, 1208 are covered with insulating coating material. In another modified embodiment, illustrated in FIG. 13B, the conductive wires 1206, 1208 are covered with insulating coating material or separated with insulating material and are contained in a unitary cable 1216. In such embodiments, the cable 1216 spirals around the central lumen 1251 along the length of the catheter 1200.

Figure 14:
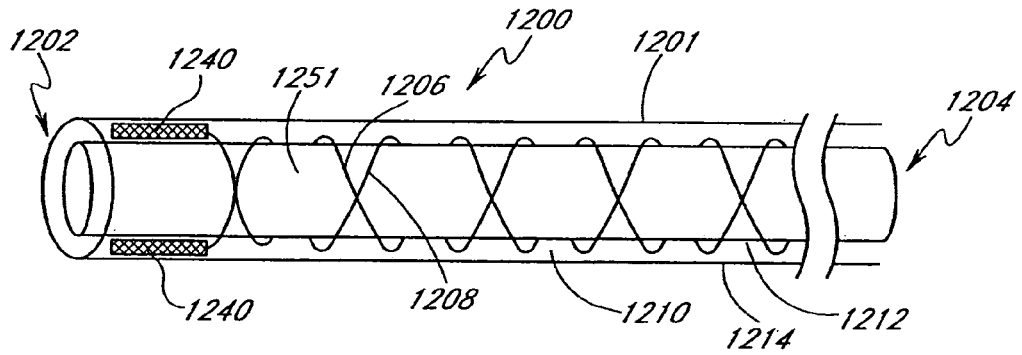
FIG. 14 is a partial cutaway view of one embodiment of an ultrasound catheter with embedded conductive wires that are spirally wrapped in a nonparallel configuration.

In another embodiment, illustrated in FIG. 14, the conductive wires 1206, 1208 are covered with insulating coating material and are spiraled in opposite directions, thereby forming a helix or helical pattern around the central lumen 1251. In forming a helical pattern, the wires 1206, 1208 cross each other, but remain electrically isolated from each other due to the insulating coating material around each wire.

Figure 15:
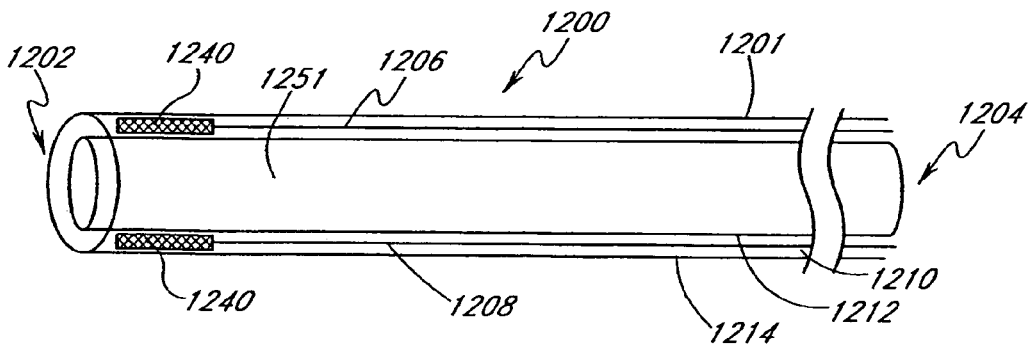
FIG. 15 is a partial cutaway view of one embodiment of an ultrasound catheter with embedded conductive wires that are disposed substantially parallel to the catheter axis.

In another embodiment, illustrated in FIG. 15, the conductive wires 1206, 1208 run in a generally straight line along the length of the catheter 1200, and do not spiral around the central lumen 1251 or cross each other. In such embodiments, the wires 12606, 12608 can optionally be covered with an insulating coating material.

In a modified embodiment, illustrated in FIGS. 16A and 16B, the ultrasound catheter comprises an outer tubular body 1400 surrounding an inner core 1402. The inner core 1402 defines a central lumen 1408 that can be used to pass a guidewire, a cooling fluid or a therapeutic compound through the ultrasonic catheter. In a distal region of the ultrasound catheter, a tubular ultrasound radiating member 1404 is positioned between the outer tubular body 1400 and the inner core 1402. In regions proximal to the ultrasound radiating member 1404, the outer tubular body 1400 and the inner core 1402 are separated by an insulating layer 1406. Preferably, the inner core outer surface 1410 and the outer tubular body inner surface 1412 are electrically conductive, and are electrically connected to opposite poles of a power supply (not shown). Such electrically conductive surfaces can be created by depositing an electrically conductive material onto the desired surface.

In such embodiments, the conductive surfaces are separated by the insulating layer 1406 along the length of the catheter, and the presence of the ultrasound radiating member 1404 in the catheter distal region completes the electric circuit. In particular, because opposite surfaces of the ultrasound radiating member contact conductive surfaces of opposite polarity 1410, 1412, a voltage difference is created across the ultrasound radiating member, thereby causing ultrasonic vibrations to be created.

Such embodiments allow the ultrasound radiating member 1404 to be driven while eliminating any wires passing along the catheter body, such as illustrated in FIGS. 13A through 15. Elimination of wiring in the catheter body reduces manufacturing costs and reduces overall catheter dimensions, thereby increasing catheter maneuverability. Elimination of wiring can also increase catheter flexibility. Thus, in applications where the ultrasound catheter is to be passed through a small or tortuous portion of the vasculature, it may be desired to use such embodiments.

Small vessel ultrasonic catheters with conducting wires or fibers embedded in the walls of the catheter, as described above, can be assembled in a number of ways. See, for example, U.S. Pat. Nos. 4,277,432 and 6,030,371, both of which are incorporated by reference herein. In one method, the catheter is made from tubing which is fabricated from a polymer material that is extruded through a dye in a molten state and that is solidified while being drawn. In one preferred embodiment of the present invention, an electrically insulating material is extruded through the dye.

Conventionally, manufacturing equipment is used to co-extrude polymer support fibers, such as, for example, Kevlar, into the tubing wall in a linear, spiral, or woven pattern. In certain embodiments of the present invention, electrically conductive wires or fibers are used in lieu of polymer support fibers. Examples of conductive fibers include, but are not limited to, copper, carbon, steel, and stainless steel. In a modified embodiment, the conductive fibers are pre-coated with an insulating coating before they are co-extruded.

In another method of assembling small vessel catheters with conducting wires or fibers embedded in the walls of the catheter, the wires are sandwiched between two concentric tubes, an inner tube and an outer tube, both of which initially have approximately half the wall thickness of the final assembled catheter. The inner diameter of the inner tube determines the diameter of the final assembled catheter. The inner diameter of the outer tube is significantly greater than the outer diameter of the inner tube. For example, the inner and outer tubes can be made from an electrically isolating material.

In such embodiments, the catheter is assembled by winding or placing conductive fiber or wire over the inner tube; concentrically translating the outer tube over the inner tube and the fiber wrapping or abutting the inner tube; and radially shrinking the outer tube onto the inner tube such that the conductive fiber is trapped between the inner and outer tubes. In a modified embodiment, the conductive fibers are pre-coated with an insulating coating before they are incorporated into the above described sandwich construction.

As described above, the various configurations and arrangements of the elongate electrical conductors described herein can be used regardless of whether such elongate electrical conductors are connected to an ultrasound radiating member or a temperature sensor at the catheter distal end.

CONCLUSION

While the foregoing detailed description has described several embodiments of the apparatus and methods of the present invention, it is to be understood that the above description is illustrative only and not limiting of the disclosed invention. It will be appreciated that the specific dimensions of the various catheters and guidewires can differ from those described above, and that the methods described can be used within any biological conduit within the body and remain within the scope of the present invention. Thus, the invention is to be limited only by the claims which follow.

We claim:

1. A method of manufacturing an ultrasonic catheter comprising:
   providing an inner tube having an inner diameter sufficient to accommodate a guidewire;
   mounting a tubular ultrasound radiating member around a distal region of the inner tube;
   positioning a first and a second electrical conductor along the inner tube, such that the first electrical conductor contacts an inner side of the ultrasound radiating member, and the second electrical conductor contacts an outer side of the ultrasound radiating member;
   concentrically translating an outer tube over the inner tube and the ultrasound radiating member; and
   radially shrinking the outer tube onto the inner tube, so that the first and the second electrical conductors are located in between the inner tube and the outer tube along the length of the ultrasonic catheter.

2. The method of claim 1, further comprising:
   mounting a temperature sensor adjacent to the distal region of the inner tube; and
   positioning at least one temperature sensor wire along the inner tube, such that the temperature sensor wire is electrically connect to the temperature sensor.

3. The method of claim 1, wherein the first and second electrical conductors are positioned along the inner tube in a substantially parallel configuration.

4. The method of claim 3, wherein the first and second electrical conductors are positioned along the inner tube at substantially radially opposite points.

5. The method of claim 1, further comprising integrating the first and second electrical conductors into a unitary cable.

6. The method of claim 1, wherein the first and second electrical conductors are wrapped around the inner core in opposite directions.

7. The method of claim 1, further comprising connecting the first and second electrical conductors to opposite poles of a power supply at a proximal end of the ultrasonic catheter.

* * * * *